United States Patent
Ogawa et al.

(10) Patent No.: US 10,585,100 B2
(45) Date of Patent: Mar. 10, 2020

(54) METHOD OF PREDICTING EFFECT OF TREATMENT BY PD-1/PD-L1 BLOCKADE USING ABNORMALITY OF PD-L1 (CD274) AS INDEX

(71) Applicants: KYOTO UNIVERSITY, Kyoto-shi, Kyoto (JP); JAPANESE FOUNDATION FOR CANCER RESEARCH, Koto-ku, Tokyo (JP)

(72) Inventors: Seishi Ogawa, Kyoto (JP); Keisuke Kataoka, Kyoto (JP); Kengo Takeuchi, Tokyo (JP)

(73) Assignees: Kyoto University, Kyoto (JP); Japanese Foundation for Cancer Research, Tokyo (JP)

( * ) Notice: Subject to any disclaimer, the term of this patent is extended or adjusted under 35 U.S.C. 154(b) by 71 days.

(21) Appl. No.: 15/569,898

(22) PCT Filed: Apr. 28, 2016

(86) PCT No.: PCT/JP2016/063326
§ 371 (c)(1),
(2) Date: Oct. 27, 2017

(87) PCT Pub. No.: WO2016/175275
PCT Pub. Date: Nov. 3, 2016

(65) Prior Publication Data
US 2018/0113131 A1     Apr. 26, 2018

(30) Foreign Application Priority Data

Apr. 30, 2015  (JP) .................................. 2015-093599

(51) Int. Cl.
| | |
|---|---|
| G01N 33/574 | (2006.01) |
| A61K 39/395 | (2006.01) |
| C12Q 1/68 | (2018.01) |
| C12N 15/09 | (2006.01) |
| A61K 45/00 | (2006.01) |
| C07K 16/28 | (2006.01) |
| C07K 16/18 | (2006.01) |

(52) U.S. Cl.
CPC ..... *G01N 33/57407* (2013.01); *A61K 39/395* (2013.01); *A61K 45/00* (2013.01); *C07K 16/2827* (2013.01); *C12N 15/09* (2013.01); *C12Q 1/68* (2013.01); *G01N 33/574* (2013.01); *G01N 33/5743* (2013.01); *G01N 33/57411* (2013.01); *G01N 33/57423* (2013.01); *G01N 33/57426* (2013.01); *G01N 33/57446* (2013.01); *C07K 16/18* (2013.01); *G01N 2333/70521* (2013.01); *G01N 2333/70532* (2013.01); *G01N 2800/52* (2013.01)

(58) Field of Classification Search
CPC ................. C07K 16/2827; G01N 2333/70532
See application file for complete search history.

(56) References Cited

U.S. PATENT DOCUMENTS

| | | |
|---|---|---|
| 2009/0217401 A1 | 8/2009 | Korman et al. |
| 2012/0094863 A1 | 4/2012 | Stroh et al. |

FOREIGN PATENT DOCUMENTS

| | | | |
|---|---|---|---|
| JP | 2006-340714 A | 12/2006 | |
| JP | 2012-529895 A | 11/2012 | |
| JP | 2016-059348 A | 4/2016 | |
| WO | WO-2014083178 A1 | * 6/2014 | ......... G01N 33/6872 |

OTHER PUBLICATIONS

International Search Report dated Jul. 5, 2016, in PCT/JP2016/063326.
Lin et al., "Programmed Death-Ligand 1 Expression Predicts Tyrosine Kinase Inhibitor Response and Better Prognosis in a Cohort of Patients with Epidermal Growth Factor Receptor Mutation-Positive Lung Adenocarcinoma," Clinical Lung Cancer, Feb. 19, 2015, 16(5):e25-35.
Schalper et al., "In Situ Pd-L1 mRNA Expression is Associated with Increased TILs and Better Outcome in Breast Carcinomas," Clinical Cancer Research, May 15, 2014 (online Mar. 19, 2014), 20(10):2773-2782.
Schultheis et al., "PD-L1 expression in small cell neuroendocrine carcinomas," European Journal of Cancer, Jan. 9, 2015, 51:421-426.
Wang et al., "A Frequent Somatic Mutation in CD2743'-UTR Leads to Protein Over-Expression in Gastric Cancer by Disrupting miR-570 Binding," Human Mutation, Dec. 2011, 33:480-484.

* cited by examiner

*Primary Examiner* — Peter J Reddig
(74) *Attorney, Agent, or Firm* — Foley & Lardner LLP

(57) ABSTRACT

An object of the present invention is to provide an effective method of predicting an effect of treatment by a PD-1/PD-L1 blockade, which is a method of predicting whether or not PD-1/PD-L1 blockade is effective for treatment of a subject suffering from a malignant tumor, which comprises detecting abnormality of genome relating to effectiveness of the PD-1/PD-L1 blockade in a tumor cell taken from the subject and evaluating the PD-1/PD-L1 blockade as useful for the treatment of the subject when there is the abnormality.

22 Claims, 28 Drawing Sheets
Specification includes a Sequence Listing.

Fig. 8

TCGA

| ACC | BLCA | BRCA | CESC | CHOL | CNTL |
|---|---|---|---|---|---|
| 79 | 414 | 1119 | 306 | 36 | 1 |
| COAD | DLBC | ESCA | GBM | HNSC | KICH |
| 486 | 48 | 185 | 170 | 522 | 66 |
| KIRC | KIRP | LAML | LGG | LIHC | LUAD |
| 542 | 291 | 179 | 534 | 374 | 541 |
| LUSC | MESO | OV | PAAD | PCPG | PRAD |
| 502 | 87 | 420 | 179 | 184 | 502 |
| READ | SARC | SKCM | STAD | TGCT | THCA |
| 167 | 263 | 472 | 420 | 156 | 513 |
| THYM | UCEC | UCS | UVM | TOTAL | |
| 120 | 557 | 57 | 80 | 10572 | |

Fig. 10
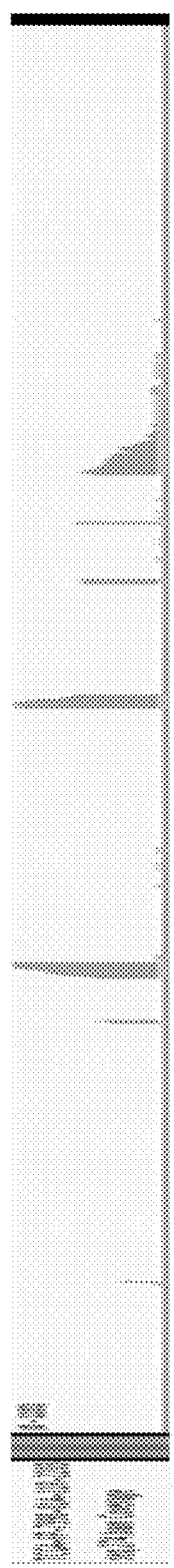
A  TCGA-FP-7998-01A-11R-2203-13 (STAD)→chr9:+5468590-chr9:-3212251 (Tandem duplication)
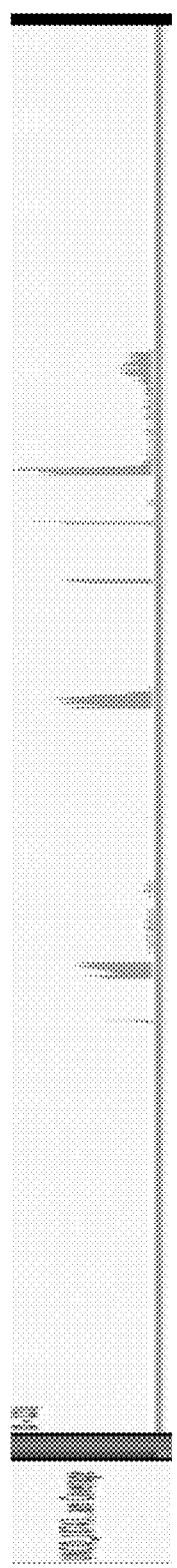
B  TCGA-AZ-4616-01A-21R-1839-07 (COAD)→ truncated at chr 9
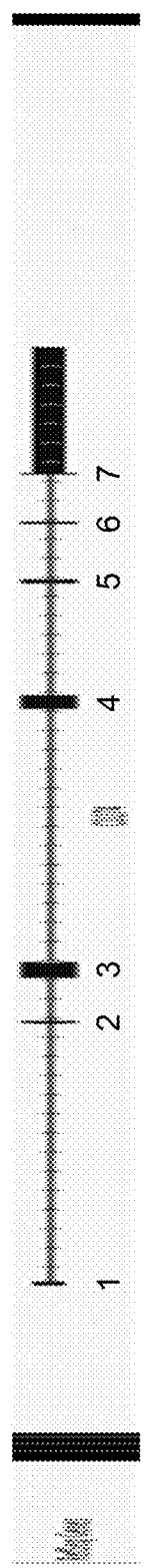

SEQUENCE LISTING

```
<160> NUMBER OF SEQ ID NOS: 13

<210> SEQ ID NO 1
<211> LENGTH: 1135
<212> TYPE: DNA
<213> ORGANISM: Homo sapiens

<400> SEQUENCE: 1
atgaggatat tgctgtctt tatattcatg acctactggc atttgctgaa cgcatttact      60
gtcacggttc ccaaggacct atatgtggta gagtatggta gcaatatgac aattgaatgc    120
aaattcccag tagaaaaaca attagacctg gctgcactaa ttgtctattg ggaaatggag    180
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg gcctccaggc ctgtgatgag agaagctgcc gtgaagacct ctgacatgcc    900
ctggagacat tttcctcatt gtcttggtga ttaacatttg gctcctcctt acttatacaa    960
atttctgcag ccagcttgag gttcttctca gagaatgtgt ttttctttt tatcacattg   1020 tcaggctgca aattttctga actttaatgc tccgcttctt cttgaaacat aagttccaat   1080
tccatatcat atctttgtga atgaataaaa cttaatgctt ttaaaaaaaa aaaaa         1135

<210> SEQ ID NO 2
<211> LENGTH: 2710
<212> TYPE: DNA
<213> ORGANISM: Homo sapiens

<400> SEQUENCE: 2
tccagcattg gaacttctga tcttcaagca gggattctca acctgtggtt tagggttca      60 tcggggctga gcgtgacaag aggaaggaat gggcccgtgg gatgcaggca atgtgggact    120
taaaaggccc aagcactgaa aatggaacct ggcgaaagca gaggaggaga atgaagaaag    180
atggagtcaa acagggagcc tggagggaga ccttgatact ttcaaatgcc tgagggctc     240 atcgacgcct gtgacaggga gaaggatac ttctgaacaa ggagcctcca agcaaatcat    300
ccattgctca tcctaggaag acgggttgag aatccctaat ttgagggtca gttcctgcag    360
aagtgccctt tgcctccact caatgcctca atttgttttc tgcatgactg agagtctcag    420
```

```
tgttggaacg ggacagtatt tatgtatgag ttttccctat ttatttgag tctgtgaggt      480 cttcttgtca tgtgagtgtg gttgtgaatg atttcttttg aagatatatt gtagtagatg      540
ttacaatttt gtcgccaaac taaacttgct gcttaatgat ttgctcacat ctagtaaaac      600
atggagtatt tgtaaggtgc ttggtctcct ctataactac aagtatacat tggaagcata      660
aagatcaaac cgttggttgc ataggatgtc acctttattt aacccattaa tactctggtt      720
gacctaatct tattctcaga cctcaagtgt ctgtgcagta tctgttccat ttaaatatca      780
gctttacaat tatgtggtag cctacacaca taatctcatt tcatcgctgt aaccaccctg      840
ttgtgataac cactattatt ttacccatcg tacagctgag gaagcaaaca gattaagtaa      900
cttgcccaaa ccagtaaata gcagacctca gactgccacc cactgtcctt ttataataca      960
atttacagct atattttact ttaagcaatt cttttattca aaaccatttt attaagtgcc     1020
cttgcaatat caatcgctgt gccaggcatt gaatctacag atgtgagcaa acaaagtac      1080 ctgtcctcaa ggagctcata gtaatgag gagattaaca agaaaatgta ttattacaat      1140
ttagtccagt gtcatagcat aaggatgatg cgaggggaaa acccgagcag tgttgccaag     1200
aggaggaaat aggccaatgt ggtctggac ggttggatat acttaaacat cttaataatc      1260
agagtaattt tcatttacaa agagaggtcg gtacttaaaa taaccctgaa aaataacact     1320
ggaattcctt ttctagcatt atatttattc ctgatttgcc tttgccatat aatctaatgc     1380
ttgtttatat agtgtctggt attgtttaac agttctgtct tttctattta aatgccacta     1440
aattttaaat tcatacctt ccatgattca aaattcaaaa gatcccatgg gagatggttg      1500
gaaaatctcc acttcatcct ccaagccatt caagtttcct ttccagaagc aactgctact     1560
gcctttcatt catatgttct tctaaagata gtctacattt ggaaatgtat gttaaaagca     1620
cgtattttta aaattttttt cctaaatagt aacacattgt atgtctgctg tgtactttgc     1680
tatttttatt tattttagtg tttcttatat agcagatgga atgaatttga agttcccagg     1740
gctgaggatc catgccttct ttgtttctaa gttatctttc ccatagcttt tcattatctt     1800
tcatatgatc cagtatatgt taaatatgtc ctacatatac atttagacaa ccaccatttg     1860
ttaagtattt gctctaggac agagtttgga tttgttatg tttgctcaaa aggagaccca     1920
tgggctctcc agggtgcact gagtcaatct agtcctaaaa agcaatctta ttattaactc     1980
tgtatgacag aatcatgtct ggaacttttg ttttctgctt tctgtcaagt ataaacttca     2040
ctttgatgct gtacttgcaa aatcacattt tcttctgga aattccggca gtgtaccttg      2100
actgctagct acccctgtgcc agaaaagcct cattcgttgt gcttgaaccc ttgaatgcca     2160
ccagctgtca tcactacaca gccctcctaa gaggcttcct ggaggtttcg agattcagat     2220
gccctgggag atcccagagt ttcctttccc tcttggccat attctggtgt caatgacaag     2280
gagtaccttg gctttgccac atgtcaaggc tgaagaaaca gtgtctccaa cagagctcct     2340
tgtgttatct gtttgtacat gtgcatttgt acagtaattg gtgtgacagt gttcttgtg      2400 tgaattacag gcaagaattg tggctgagca aggcacatag tctactcagt ctattcctaa     2460
gtcctaactc ctccttgtgg tgttggattt gtaaggcact ttatcccttt tgtctcatgt     2520
ttcatcgtaa atggcatagg cagagatgat acctaattct gcatttgatt gtcacttttt     2580
gtacctgcat taatttaata aaatattctt atttattttg ttacttggta caccagcatg     2640 tccatttct tgtttatttt gtgtttaata aaatgttcag tttaacatcc cagtggagaa      2700
agttaaaaaa                                                           2710
```

```
<210> SEQ ID NO 3
<211> LENGTH: 50
<212> TYPE: PRT
<213> ORGANISM: Homo sapiens

<400> SEQUENCE: 3

Leu Val Ile Leu Gly Ala Ile Leu Leu Cys Leu Gly Val Ala Leu Thr
1               5                   10                  15

Phe Ile Phe Arg Leu Arg Lys Gly Arg Met Met Asp Val Lys Lys Cys
            20                  25                  30

Gly Ile Gln Asp Thr Asn Ser Lys Lys Gln Ser Asp Thr His Leu Glu
        35                  40                  45

Glu Thr
    50

<210> SEQ ID NO 4
<211> LENGTH: 61
<212> TYPE: PRT
<213> ORGANISM: Homo sapiens

<400> SEQUENCE: 4

Leu Val Ile Leu Gly Ala Ile Leu Leu Cys Leu Gly Val Ala Leu Thr
1               5                   10                  15

Phe Ile Phe Arg Leu Arg Lys Gly Arg Met Met Asp Val Lys Lys Cys
            20                  25                  30

Gly Ile Gln Asp Thr Asn Ser Lys Lys Gln Ser Ala Glu Thr Gly Phe
        35                  40                  45

His Cys Val Ser Gln Asp Gly Leu Asn Leu Leu Thr Ser
    50                  55                  60

<210> SEQ ID NO 5
<211> LENGTH: 75
<212> TYPE: PRT
<213> ORGANISM: Homo sapiens

<400> SEQUENCE: 5

Leu Val Ile Leu Gly Ala Ile Leu Leu Cys Leu Gly Val Ala Leu Thr
1               5                   10                  15

Phe Ile Phe Arg Leu Arg Lys Gly Arg Met Met Asp Val Lys Lys Cys
            20                  25                  30

Gly Ile Gln Asp Thr Asn Ser Lys Lys Gln Ser Asp His Pro Gly Ser
        35                  40                  45

His His Ser Pro Ala Ser Val Ser Arg Val Ala Gly Thr Thr Gly Ala
    50                  55                  60

His His His Ala Gln Gln Ile Phe Cys Val Phe
65                  70                  75

<210> SEQ ID NO 6
<211> LENGTH: 57
<212> TYPE: PRT
<213> ORGANISM: Homo sapiens

<400> SEQUENCE: 6

Leu Val Ile Leu Gly Ala Ile Leu Leu Cys Leu Gly Val Ala Leu Thr
1               5                   10                  15

Phe Ile Phe Arg Leu Arg Lys Gly Arg Met Met Asp Val Lys Lys Cys
            20                  25                  30

Gly Ile Gln Asp Thr Asn Ser Lys Lys Gln Ser Gly Leu Gln Ala Cys
        35                  40                  45
```

Asp Glu Arg Ser Cys Arg Glu Asp Leu
        50                  55

<210> SEQ ID NO 7
<211> LENGTH: 39
<212> TYPE: PRT
<213> ORGANISM: Homo sapiens

<400> SEQUENCE: 7

Leu Val Ile Leu Gly Ala Ile Leu Leu Cys Leu Gly Val Ala Leu Thr
1               5                   10                  15

Phe Ile Phe Arg Leu Arg Lys Asp Trp Glu Arg Asp Phe His Met Asn
            20                  25                  30

Cys Leu Gln Ile Pro Arg Glu
        35

<210> SEQ ID NO 8
<211> LENGTH: 36
<212> TYPE: PRT
<213> ORGANISM: Homo sapiens

<400> SEQUENCE: 8

Leu Val Ile Leu Gly Ala Ile Leu Leu Cys Leu Gly Val Ala Leu Thr
1               5                   10                  15

Phe Ile Phe Arg Leu Arg Lys Gly Ala Glu Gly Leu Ser Gln Leu Ser
            20                  25                  30

Pro Gln Leu Leu
        35

<210> SEQ ID NO 9
<211> LENGTH: 37
<212> TYPE: PRT
<213> ORGANISM: Homo sapiens

<400> SEQUENCE: 9

Leu Val Ile Leu Gly Ala Ile Leu Leu Cys Leu Gly Val Ala Leu Thr
1               5                   10                  15

Phe Ile Phe Arg Leu Arg Lys Asp Arg Asp Lys Arg Lys Thr Ala Asn
            20                  25                  30

Thr Gly Arg Gly Leu
        35

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
ggcatccaag atacaaactc aa                                          22

<210> SEQ ID NO 11
<211> LENGTH: 22
<212> TYPE: DNA
<213> ORGANISM: Artificial
<220> FEATURE:
<223> OTHER INFORMATION: Primer

<400> SEQUENCE: 11
cagaagttcc aatgctggat ta                                          22

```
<210> SEQ ID NO 12
<211> LENGTH: 40
<212> TYPE: DNA
<213> ORGANISM: Artificial
<220> FEATURE:
<223> OTHER INFORMATION: Synthetic

<400> SEQUENCE: 12
acacagctga tcacaaaaat gtaaaacata aaagtgcaat                              40

<210> SEQ ID NO 13
<211> LENGTH: 40
<212> TYPE: DNA
<213> ORGANISM: Artificial
<220> FEATURE:
<223> OTHER INFORMATION: Synthetic

<400> SEQUENCE: 13
aaactcaaag aagcaaagtg gtaagaatat cagaaggaat                              40
```

METHOD OF PREDICTING EFFECT OF TREATMENT BY PD-1/PD-L1 BLOCKADE USING ABNORMALITY OF PD-L1 (CD274) AS INDEX

CROSS-REFERENCE TO RELATED APPLICATIONS

This application is a National Stage application of PCT/JP2016/063326, filed Apr. 28. 2016, which claims priority from Japanese application JP2015-093599, filed Apr. 30, 2015.

Technical Field

The present invention relates to a method of predicting an effect of treatment by a PD-1/PD-L1 blockade such as anti PD-1 antibody by examining the presence or absence of an abnormality of PD-L1 gene in a tumor cell.

Sequence Listing

The present application contains a Sequence Listing which has been submitted electronically in ASCII format and is hereby incorporated by reference in its entirety. The ASCII copy, created on Apr. 26, 2016, is named PH-6552-PCT_SL.txt and is 10,000 bytes in size.

Background Art

Recently, it has been elucidated that a PD-1/PD-L1 blockade is effective for various types of malignant tumors including metastatic malignant melanoma, renal cancer, lung cancer and Hodgkin's disease. As the PD-1/PD-L1 blockade, an anti PD-1 monoclonal antibody, i.e., Nivolumab, has been put into practical use (see, Patent Literature 1). At present, searching a biomarker for predicting an effect of treatment by this blockade is an urgent issue. It has been found that the efficacy rate is high when "PD-L1 positive" is found by immunostaining in tumor cells and peripheral immune cells. However, evaluation of PD-L1 positive rate by immunostaining is not sufficient in view of sensitivity/specificity. It is desired that prediction on efficacy of therapy is further improved.

It has been increasingly clear that a PD-1/PD-L1 blockade is effective in many malignant tumors. Of them, malignant tumors on which the blockade less effectively works are included. However, even in such tumors, a case having a structural abnormality of PD-L1 accompanied by high expression thereof is likely to be present. However, a useful method for sorting out a case where a PD-1/PD-L1 blockade possibly works has not yet been established.

CITATION LIST

Patent Literature

Patent Literature 1: JP Patent Publication (Kokai) No. 2006-340714

SUMMARY OF INVENTION

Technical Problem

An object of the present invention is to provide an effective method for predicting an effect of treatment by a PD-1/PD-L1 blockade. Another object is to develop a platform for sorting out a case on which these blockades effectively work with a high probability even in tumors to which a PD-1/PD-L1 blockade has not yet been applied, and then applying a treatment to the case.

Solution to Problem

The present inventors conducted comprehensive gene analysis (RNA sequencing: 57 cases, whole genome sequencing: 11 cases) of adult T cell leukemia/lymphoma (ATL). Based on the gene analysis, they clarified that a structural abnormality of PD-L1 (CD274) is present in about 20% of ATL cases. Examples of the structural abnormality include all structural abnormalities such as deletion, tandem duplication, inversion and translocation. These structural abnormalities commonly have a deletion of 3'UTR. Furthermore in all cases having a structural abnormality, a remarkable increase of PD-L1 mRNA level was observed and an increase of PD-L1 protein expression on the cell surface was confirmed by flow cytometry. Moreover, studies were conducted on the presence of the same abnormality in other cancers based on TCGA data. As a result, it was found that the same abnormality is present in various types of malignant tumors such as stomach cancer, lung cancer, large intestinal cancer, cervical cancer, malignant melanoma and B cell lymphoma. This result suggests that a structural abnormality, i.e., a deletion of 3'UTR of PD-L1 accompanied by high expression of PD-L1 is a common abnormality occurring in various types of malignant tumors.

Based on these results, the present inventors found that the effect of a PD-1/PD-L1 blockade can be determined and evaluated based on a deletion of 3'UTR in PD-L1 gene as an index and accomplished the present invention.

More specifically, the present invention is as follows.
[1] A method of predicting whether or not PD-1/PD-L1 blockade is effective for treatment of a subject suffering from malignant tumor, which comprises detecting abnormality of genome relating to effectiveness of the PD-1/PD-L1 blockade in a tumor cell taken from the subject and evaluating the PD-1/PD-L1 blockade as useful for the treatment of the subject when there is the abnormality.
[2] The method according to [1], wherein the abnormality of genome relating to effectiveness of the PD-1/PD-L1 blockade is abnormality of PD-L1 gene relating to the acceleration of the expression of PD-L1 (CD274) gene.
[3] The method according to [2], wherein the abnormality of PD-L1 gene is partial or complete deletion of 3'UTR region of PD-L1 gene.
[4] The method according to [2], wherein the abnormality of PD-L1 gene is change in copy number which induces deletion of 3'UTR region of PD-L1 gene.
[5] The method according to [2], wherein the abnormality of PD-L1 gene is complete or partial truncation of exon 5, exon 6 and exon 7 from PD-L1 transcript.
[6] The method according to [2], wherein the abnormality of PD-L1 gene is complete or partial truncation of exon 5, exon 6 and exon 7 from PD-L1 transcript.
[7] The method according to [2], which comprises quantifying a transcript of any one of exon 1 to exon 4 of PD-L1 gene and a transcript of 3'UTR region of PD-L1 gene and calculating a ratio between the amount of the transcript of the exon and the amount of the transcript of the 3'UTR region, and evaluating the PD-1/PD-L1 blockade as useful for the treatment of cancer when the ratio is not less than a predetermined value.

[8] The method according to [2], wherein the abnormality of PD-L1 gene is acceleration of the expression of PD-L1 mRNA.

[9] The method according to [2], wherein the abnormality of PD-L1 gene is the abnormality caused by the insertion of a virus.

[10] The method according to [9], wherein the virus is Human papilloma virus (HPV) or EBV (Epstein-barr virus).

[11] The method according to [2], which comprises staining a PD-L1 protein in a tumor cell taken from the subject by immunohistochemical staining using an antibody against a C terminal region of PD-L1 and an antibody against a N terminal region of PD-L1, and evaluating the PD-1/PD-L1 blockade as useful for the treatment of the subject when the tumor cell becomes stained with the antibody against a N terminal region of PD-L1 but the tumor cell does not become stained with the antibody against a C terminal region of PD-L1.

[12] The method according to any one of [1] to [11], wherein the malignant tumor is selected from the group consisting of adult T-cell leukemia/adult T-cell leukemia lymphoma, stomach cancer, large intestinal cancer, bladder cancer, cervical cancer, renal cancer, lung adenocarcinoma, cutaneous malignant melanoma, and B cell lymphoma.

[13] The method according to any one of [1] to [11], wherein the malignant tumor is selected from the group consisting of esophageal cancer, head and neck cancer, and uterine body cancer.

[14] The method according to any one of [1] to [13], wherein the PD-1/PD-L1 blockade is anti PD-1 antibody or anti PD-L1 antibody.

[15] A treatment method comprising detecting an abnormality of genome relating to effectiveness of a PD-1/PD-L1 blockade in a tumor cell taken from a subject suffering from a malignant tumor and applying a treatment with the PD-1/PD-L1 blockade when the abnormality is present.

Advantageous Effects of Invention

As shown in Examples, in various malignant tumors, there are cases where PD-L1 is highly expressed due to a structural abnormality of PD-L1 gene. More specifically, a structural abnormality of PD-L1 (mainly serving as an immune checkpoint) and the resulting fusion gene with a non-coding region were identified as a gene abnormality in various types of malignant tumors beyond ordinal expectation. In consideration that an anti PD-1/PD-L1 blockade is overwhelmingly effective (efficacy rate: about 90%) in a preclinical study (mouse model) of this research and in Hodgkin's disease, which is known as only one case where PD-L1 is constantly activated by a genomic abnormality, it is expected that an anti PD-1/PD-L1 blockade is extremely effective for patients having a PD-L1 structural abnormality and becomes a prospective biomarker. Accordingly, the genetic abnormality directly relating to an effective treatment is an extremely prospective target for clinical examination.

As to a malignant tumor to which a PD-1/PD-L1 blockade is already applied, an effect of treatment by the PD-1/PD-L1 blockade can be successfully predicted based on detection of a PD-L1 structural abnormality. Also, even in the cases of tumors to which a PD-1/PD-L1 blockade has not yet been applied, if an abnormality of PD-L1 gene is present therein, the PD-1/PD-L1 blockade is likely to be effective. If such a case is sorted out, a novel therapy can be possibly established. In addition, if a clinical trial is carried out based on a structural abnormality of PD-L1 as an index, the number of diseases for which it is indicated can be effectively increased. This means that the range of the indication is not limited to malignant tumors, for which the indication has been approved or under consideration, and can be enlarged to malignant tumors, for which effectiveness of the blockage is in general regarded as being insufficient.

BRIEF DESCRIPTION OF DRAWINGS

FIG. 8 shows analysis results of CD274 structural abnormality and expression in various types of cancers based on TCGA data.

In FIG. 9, SKCM represents skin cutaneous melanoma (FIG. 9A), COADREAD colorectal adenocarcinoma, (FIG. 9B), STAD stomach adenocarcinoma (FIG. 9C) and DLBC diffuse large B-cell lymphoma (FIG. 9D).

FIG. 10 shows analysis results (I) of CD274 expression in various types of malignant tumors based on TCGA data. FIG. 10A shows the result of stomach adenocarcinoma (STAD) and FIG. 10B shows the result of colon adenocarcinoma (COAD).

In FIG. 11, two cases of diffuse large B-cell lymphoma (DLBC) were similarly shown as an example (FIGS. 11A and B).

FIG. 17A shows the verification results of a VS-A9U7-01 case (CESC) and FIG. 17B shows a FP-7998-01 case (STAD).

FIG. 20-1 shows a protocol of an experiment evaluating the effect of high expression of CD274 in association with a CD274 3'UTR abnormality on tumorigenic potential.

FIG. 20-2 shows the effect of high expression of CD274 in association with a CD274 3'UTR abnormality on tumorigenic potential. A change in tumor diameter of Mock is shown in FIG. 20-2A and a change in tumor diameter of EG7-OVA cell line (SgPD-L1), in which high expression of CD274 was induced, is shown in FIG. 20-2B.

FIG. 21-1 shows stained images showing that high expression of CD274 in association with a CD274 3'UTR abnormality suppresses infiltration of CD8 positive T cells into a tumor.

FIG. 21-2 is a graph (the number of cells) showing that high expression of CD274 in association with a CD274 3'UTR abnormality suppresses infiltration of CD8positive T cell into a tumor.

FIG. 22-1 is a graph showing the effect of a PD-1/PD-L1 blockade against tumorigenic potential due to high expression of CD274 in association with a CD274 3'UTR abnormality, based on a time-dependent change of a tumor in diameter.

FIG. 22-2 shows the effect of a PD-1/PD-L1 blockade against tumorigenic potential due to high expression of CD274 in association with a CD274 3'UTR abnormality, based on immunostaining. An anti PD-L1 antibody was administered (FIG. 22-2B) or an isotype control was administered (FIG. 22-2A).

FIG. 22-3 shows the effect of a PD-1/PD-L1 blockade against tumorigenic potential due to high expression of CD274 in association with a CD274 3'UTR abnormality, based on the number of cells.

FIG. 23A shows the evaluation results of ATL patient's specimens and FIG. 23B shows the results of the PC-9 cell line.

FIG. 24A shows the results of DLBC (B cellular lymphoma), FIG. 24B shows the results of STAD (stomach adenocarcinoma). and FIG. 24C shows the results of ATL (adult T cell leukemia).

DESCRIPTION OF EMBODIMENTS

Figure 1:
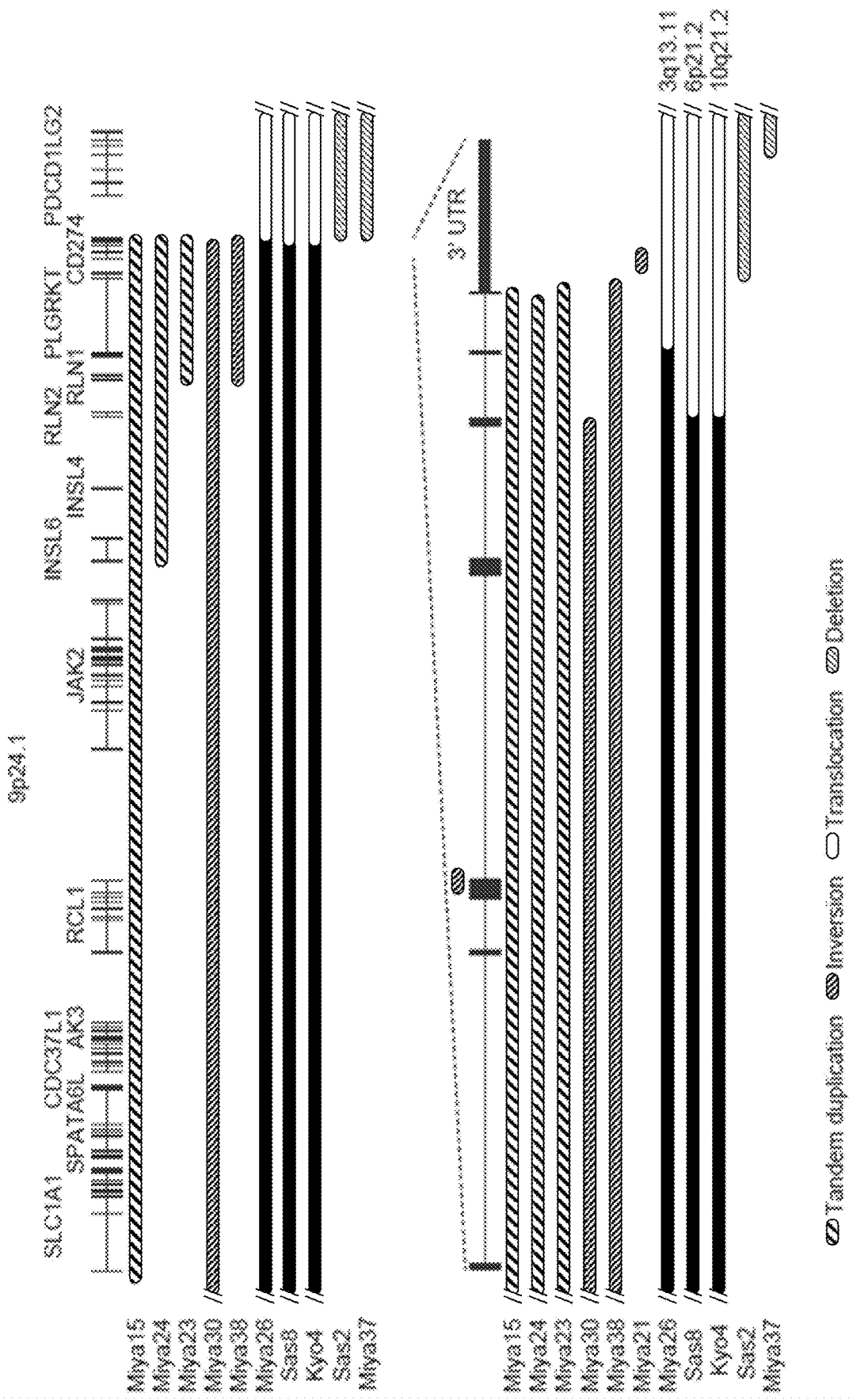
FIG. 1 shows the search results for structural abnormality in 9p24.1 region in RNA sequencing (57 cases) and whole genome sequencing (11 cases).

Now, the present invention will be more specifically described, below.

The present invention relates to a method of evaluating and determining the effectiveness of a PD-1/PD-L1 blockade in a patient with a malignant tumor, based on a genomic abnormality relating to effectiveness of the PD-1/PD-L1 blockade in the patient as an index, or a method of obtaining supportive data for evaluating and determining the effectiveness of a PD-1/PD-L1 blockade in the patient. In the present invention, evaluation/determination is also referred to as prediction. PD-L1 is also referred to as CD274 or B7-H1.

The genomic abnormality relating to effectiveness of a PD-1/PD-L1 blockade herein refers to an abnormality, which is found in the genome of a patient with a malignant tumor and on which a PD-1/PD-L1 blockade has a high effect. Examples of such an abnormality include an abnormality of chromosome 9p24.1, on which PD-L1 gene is present, and an abnormality of PD-L1 gene. Such an abnormality is referred to also as a structural variation (SV) of PD-L1 gene. With these abnormalities, abnormal expression of PD-L1 can be induced in tumor cells of a patient with a malignant tumor. Examples of the genomic abnormality relating to effectiveness of a PD-1/PD-L1 blockade include structural abnormalities such as tandem duplication, deletion, inversion and translocation of a gene; abnormalities in number of copies such as an increase or decrease in number and uniparental disomy; and qualitative (deletion of 3'UTR) and quantitative abnormalities of an expression product and a transcript product. The PD-L1 abnormal expression in tumor cells refers to acceleration of PD-L1 gene expression compared to that in cells of a healthy person or that in tumor cells having a normal PD-L1 gene; more specifically, to the case where the expression of PD-L1 at an mRNA or protein level is 5 times or more, preferably 10 times or more, further preferably 20 times or more, and further preferably 50 times or more as high as normal cases. If abnormal expression of PD-L1 is detected, it is possible to predict that genomic abnormality relating to effectiveness of a PD-1/PD-L1 blockade is present.

In a living body, T cells have an immune function against a tumor (i.e., T cells attack tumor cells). However, when PD-L1 ligand expressed by a tumor cell binds to PD-1 (Programmed cell death 1) expressed by a T cell, cell death of the T cell is induced, with the result that the immune function against a tumor is suppressed. A PD-1/PD-L1 blockade blocks binding of PD-L1 of a tumor cell and PD-1 of a T cell, thereby suppressing the immune function of the T cell against a tumor. Examples of the PD-1/PD-L1 blockade include anti PD-1 antibody and anti PD-L1 antibody. Examples of the anti PD-1/PD-L1 antibody used as a cancer drug include Nivolumab, MPDL3280A, pembrolizumab (MK-3475), MEDI4736, MSB0010718C, Pidilizumab and MEDI0680. A PD-1/PD-L1 blockade highly effectively works in the case of a patient where PD-L1 is highly expressed in tumor cells and peripheral immune cells. Accordingly, if the expression level of PD-L1 is measured, the effectiveness of a PD-1/PD-L1 blockade can be determined. For example, expression of PD-L1 in a tumor cell can be checked by immunostaining; however, evaluation of a PD-L1 positive rate by immunostaining is not sufficient in view of sensitivity and specificity.

Whether genomic abnormality in a patient with a malignant tumor relates to the effectiveness of a PD-1/PD-L1 blockade in tumor cells can be found just by investigating whether genomic abnormality relates to acceleration of PD-L1 gene expression; more specifically, can be determined by comprehensively analyzing structural abnormalities of the whole genome in the tumor cell, at the same time, determining PD-L1 gene expression in the tumor cell at an mRNA level or protein level and associating a genomic (structural) abnormality with acceleration of the PD-L1 gene expression. Further more specifically, DNA is isolated from a tumor cell and the whole genome is sequenced and analyzed for genomic structural abnormalities such as tandem duplication, inversion, translocation and deletion; at the same time, the total RNA of the tumor cell is sequenced and PD-L1 gene expression is determined; and then, association of a genomic abnormality with the PD-L1 gene expression may be analyzed. For example, in a number of tumor cells having a certain genomic abnormality, if acceleration of PD-L1 gene expression is found, it can be determined that the abnormality is associated with acceleration of the PD-L1 gene expression and relates to the effectiveness of a PD-1/PD-L1 blockade.

Actually, when PD-L1 gene expression is accelerated by a genomic abnormality, apoptosis of T cells expressing PD-1 is induced. Also when PD-L1 gene expression is accelerated by a genomic abnormality, infiltration of CD8 positive cytotoxic T cells into a tumor is suppressed and tumor growth is accelerated. Furthermore, immunity escape due to PD-L1 genomic abnormality is suppressed by anti PD-1/PD-L1 block.

The type of tumor, to which the method of the present invention of evaluating and determining the effectiveness of a PD-L1/PD-1 blockade can be applied, is not limited. At least, adult T cell leukemia/lymphoma, stomach cancer, large intestine cancer, bladder cancer, cervical cancer, renal cancer, lung adenocarcinoma, skin malignant melanoma, B cell lymphoma, esophageal cancer, head and neck cancer and uterine body cancer, are mentioned. The large intestinal cancer includes colon cancer and rectal cancer.

In the method of the present invention, a tumor specimen is taken from a subject suffering from a malignant tumor and tumor cells of the specimen may be subjected to genomic abnormality analysis.

In the method of the present invention, as specific example of the analysis object, i.e., genomic abnormality relating to effectiveness of a PD-1/PD-L1 blockade, the following abnormalities are mentioned.

(1) Genomic Abnormality Having a 3'UTR (3' Untranslated Region) Deletion of PD-L1 Gene PD-L1 gene is present in 9p24.1 region. Examples of the structural abnormality of the gene include tandem duplication, inversion, translocation and deletion. When 3'UTR has a deletion due to structural abnormality of PD-L1 gene, PD-L1 is highly expressed. This is because 3'UTR is a region that plays an important role in keeping stability and regulating translation of mRNA, and if this region is deleted, the gene loses these functions. The deletion of 3'UTR in PD-L1 gene includes a complete deletion and a partial deletion. Examples of the abnormality in number of copies (CNV) of 9p24.1 region including PD-L1 gene include an increase and decrease in copy number and uniparental disomy. The abnormality in number of copies occurs in association with structural abnormality. When a deletion in the 3'UTR occurs, PD-L1 is highly expressed.

The PD-L1 gene having 3'UTR deleted is partly truncated in the middle of an exon region, with the result that a different protein from a wild-type PD-L1 is produced. PD-L1 (protein) consists of three domains, i.e., an extracellular domain, a transmembrane domain and a cytoplasmic domain. In binding to PD-1, the extracellular domain and transmembrane domain are participated. Even if the PD-L1 gene is truncated in the middle of the exon region, PD-L1 keeps a binding ability to PD-1. More specifically, even if PD-L1 gene is truncated in the middle of the exon region, as long as it has the extracellular domain and transmembrane domain, PD-L1 has a function suppressing antitumor immunity. Accordingly, regardless of whether the PD-L1 protein is truncated or not, a tumor cell highly expressing PD-L1 protein due to genomic abnormality of PD-L1 gene is blocked in the function of suppressing tumor immunity by a PD-1/PD-L1 blockade. Accordingly, blocking of the PD-1/PD-L1 is effective for treating a malignant tumor having a genomic abnormality of PD-L1 gene.

The nucleotide sequence of PD-L1 gene is registered under NM_014143. The nucleotide sequence of 3'UTR of PD-L1 gene is represented by SEQ ID No: 2.

(2) Abnormality in Transcript and Translated Product of PD-L1 Gene

As abnormality of PD-L1 mRNA, whole or partial truncation of 3'UTR of mRNA and accompanying high expression are mentioned. In addition, a truncation on or downstream of exon 5 or 6 may sometimes be present. As the truncation of exon, a truncation of a whole region of exon 6 and exon 7, a truncation of the whole exon 7 and a truncation in the middle of exon 7. In the present invention, such a truncation of exon refers to a truncation of exon 6 or a whole or partial truncation of exon 7. Further, a truncation on and downstream of exon 4, more specifically, a truncation of the whole region of exon 5, exon 6 and exon 7 may occur.

As abnormality of PD-L1 protein, high expression is mentioned. The high expression of PD-L1 protein occurs independent of an increase of PD-L1 gene in number of copies and relates to structural abnormality of PD-L1 gene. Since exon 5 or 6 constitutes the cytoplasmic domain of PD-L1 protein, if a deletion on and downstream exon 4 is present, the abnormality of PD-L1 protein includes a partial deletion of the cytoplasmic domain.

A carcinogenic virus such as HPV (e.g., Human papilloma virus (HPV) 16) and EBV (Epstein-barr virus), if it is introduced into PD-L1 gene region, sometimes induces a structural abnormality. For example, in some cases where Human papilloma virus (HPV) in inserted into intron 6 of PD-L1 gene and Epstein-Barr virus (EBV) gene is inserted in an upstream gene region adjacent to PD-L1 gene and located upstream thereof, a PD-L1 transcript is truncated at 3'UTR.

Genomic abnormality relating to effectiveness of a PD-1/PD-L1 blockade can be analyzed in accordance with a general method for analyzing genomic structural abnormality and gene abnormality using tumor cells taken from a patient with a malignant tumor. Examples of the analysis method include an analysis method based on sequence analysis by extracting DNA or RNA from tumor cells and directly determining the sequence thereof by a method known in the art such as the PCR/Sanger sequence method, dideoxy method and Maxam-Gilbert method; an analysis method for global gene including a whole genome sequencing, whole exon sequencing and a target sequencing by a next generation sequencer; a FISH (fluorescence in situ hybridization) method; a hybridization method using a specific probe to a region having a gene abnormality or a microarray (DNA chip) having a specific probe immobilized therein, such as a copy number analysis method using e.g., an SNP array and a CGH array; and methods using a specific primer to a region having a gene abnormality. Examples of the method using a primer include PCR method, NASBA method, LCR method, SDA method, LAMP method, a method using restriction fragment length polymorphism (RFLP) and a primer extension method (TaqMan (registered trade mark) method). As the next generation sequencer, e.g., Genome Sequencer FLX (GD FLX) (Roche) and Illumina HiSeq/MiSeq (Illumina) can be used.

A deletion in 3'UTR of PD-L1 gene can be detected by a method using a probe and/or a primer as well as by RNA sequencing and a FISH method.

A deletion of 3'UTR in mRNA can be detected by calculating the ratio of transcript amount of exons (exon 1 to 5) of PD-L1 gene having no deletion and the transcript amount of 3'UTR. More specifically, mRNA of any one of exons 1 to 5 of PD-L1 gene, for example, exon 3 or exon 4 and mRNA of 3'UTR region are quantified by RNA sequencing and quantitative PCR and the ratio of expression of exon 3 or exon 4/3'UTR expression is calculated. In this manner, the presence or absence of 3'UTR expression, more specifically, the presence or absence of 3'UTR deletion, can be determined. If the ratio is high, it can be determined that 3'UTR is deleted. The case where the ratio of exon 3 expression/3'UTR expression is large refers to the case where exon 3 expression/3'UTR expression is large relative to exon 3 expression/3'UTR expression in a tumor cell having no abnormality of PD-L1 gene; for example, refers to the case where the ratio of the exon 3 expression/3'UTR expression is a predetermined value or more, more specifically, double or more, preferably 3 times or more, further preferably 5 times or more. Similarly, the case where the ratio of exon 4 expression/3'UTR expression is large refers to the case where exon 4 expression/3'UTR expression is larger relative to exon 4 expression/3'UTR expression in a tumor cell having no abnormality of PD-L1 gene, for example, refers to the case where the ratio of exon 4 expression/3'UTR expression is a predetermined value or more, more specifically, double or more, preferably 3 times or more, further preferably 5 times or more.

The abnormal PD-L1 gene expression can be detected by measuring PD-L1 mRNA in a tumor cell by use of a (semi) quantitative PCR, such as RQ-PCR and RT-PCR. RQ-PCR is a method of continuously detecting accumulation of a PCR product during a PCR process, thereby enabling easy and accurate quantification in the exponential phase in the beginning of PCR.

The probe or primer to be used in the above methods, consists of a nucleotide fragment (preferably a DNA fragment) consisting of a nucleotide sequence containing a genomic abnormality site relating to acceleration of PD-L1 gene expression; a nucleotide sequence complementary to the nucleotide sequence or a sequence capable of hybridizing with either one of these sequences under stringent conditions. The number of bases is 5 to 50, preferably 10 to 30 and further preferably 10 to 25.

In the case of having a deletion on and downstream of exon 4, more specifically, a deletion of the C terminal region of PD-L1 protein due to a structural abnormality of PD-L1 gene, more specifically a case having a truncated ORF, the abnormal protein expressed reacts with an antibody against the C terminal region of PD-L1 protein (antibody against the C terminal of PD-L1) and does not react with an antibody against the N terminal region of PD-L1 protein (antibody against the N terminal of PD-L1). Accordingly, if the antibody against the C terminal of PD-L1 and the antibody against the N terminal of PD-L1 are used to examine the reactivity between both antibodies and the PD-L1 protein produced, the structural abnormality of PD-L1 gene can be identified. More specifically, for example, PD-L1 protein in a tumor cell is stained with an antibody against the C terminal of PD-L1 and an antibody against the N terminal of PD-L1, which are stained with e.g., a fluorescence dye, to visualize the PD-L1 protein. If the protein is stained with the anti N terminal antibody but not stained with the anti C terminal antibody, it can be determined that the PD-L1 gene has a structural abnormality.

When presence of an abnormality of PD-L1 gene relating to acceleration of PD-L1 gene expression in a tumor cell taken from a subject is found by the method of the present invention, it is possible to evaluate and determine that a PD-1/PD-L1 blockade has an effect on a malignant tumor of a subject with a high probability. Also, in a tumor cell of a malignant tumor, if the presence of abnormality of PD-L1 gene relating to acceleration of PD-L1 gene expression is found, it is possible to evaluate and determine that a PD-1/PD-L1 blockade has an effect on the malignant tumor with a high probability.

It is considered that the percentage of patients to which a PD-1/PD-L1 blockade effectively works varies depending upon the type of malignant tumor. For example, in adult T cell leukemia/lymphoma, stomach cancer, large intestinal cancer, bladder cancer, cervical cancer, renal cancer, lung cancer, skin malignant melanoma, B cell lymphoma, esophageal cancer, head and neck cancer and uterine body cancer, if a transcript has a 3'UTR abnormality, expression of PD-L1 is known to be accelerated. With respect to patients suffering from these malignant cancers, whether a PD-1/PD-L1 blockade is effective or not can be evaluated by the method of the present invention. Furthermore, with respect to patients suffering from the other malignant tumors, whether a PD-1/PD-L1 blockade is effective or not can be evaluated by the method of the present invention.

Moreover, for example, in adult T cell leukemia and, stomach cancer, the ratio of the patients on which a PD-1/PD-L1 blockade effectively works is high but it is possible that the ratio is low in e. g., malignant melanoma, lung cancer and renal cancer. The method of the present invention not only enables to evaluate and determine the effectiveness of a PD-1/PD-L1 blockade on the patients suffering from a malignant tumor (the ratio of patients effectively treated with a PD-1/PD-L1 blockade is high) but also enables to evaluate and determine the effectiveness of a PD-1/PD-L1 blockade on the patients suffering from a malignant tumor (the ratio of patients effectively treated with a PD-1/PD-L1 blockade is low and a PD-1/PD-L1 is not conventionally applied).

More specifically, the present invention relates to a method of predicting whether or not a PD-1/PD-L1 blockade is effective for treating a subject suffering from a malignant tumor, and includes a method comprising detecting genomic abnormality relating to effectiveness of a PD-1/PD-L1 blockade in a tumor cell taken from a subject suffering from a malignant tumor on which a PD-1/PD-L1 blockade have a low effect and evaluating that the PD-1/PD-L1 blockade is effective for treating the subject when an abnormality is present, thereby expanding the range of the indication for the PD-1/PD-L1 blockade to the tumor on which the PD-1/PD-L1 blockade has a low effect.

As mentioned above, the method of the present invention enables to evaluate and determine whether a PD-1/PD-L1 blockade is effective or not for various types of malignant tumors or patients suffering from various types of malignant tumors and enables to select an appropriate treatment method for a patient.

If an abnormality of PD-L1 gene relating to acceleration of the PD-L1 gene expression is found in tumor cells taken from a subject, and if a PD-1/PD-L1 blockade can be evaluated and determined to effectively treat a malignant tumor of the subject with a high probability, an immune checkpoint blockade such as a PD-1/PD-L1 blockade containing an anti PD-1 monoclonal antibody or an anti PD-L1 monoclonal antibody may be administered to the subject.

The dosage varies depending on e.g., the age, body weight and symptom. The dosage of 0.001 mg to 100 mg per dose may be administered by parenteral administration such as intravenous injection, intraperitoneal injection, subcutaneous injection and intramuscular injection or oral administration at intervals of several days, several weeks or several months. The blockade to be administered may contain a pharmacologically acceptable carrier, diluent or excipient. The dosage form of the blockade is not limited, a dosage form for oral administration such as a tablet, a capsule, a granule, a powder and a syrup, or a dosage form for parenteral administration such as an injection, a drip, a suppository and a spray may be mentioned.

EXAMPLES

The present invention will be more specifically described by way of the following Examples; however, the present invention is not limited by these Examples.

1. Search for Structural Abnormality in 9p24.1 Region in RNA Sequencing (57 Cases) and Whole Genome Sequencing (11 Cases)
(Method)

RNA sequencing of 57 tumor specimens of ATL (adult T cell leukemia) and total genome sequencing of tumor-normal (buccal mucosa) pairs of ATL (11 cases) were performed.

RNA of tumor specimens was extracted by the RNeasy Mini kit (QIAGEN) and RINe was measured by the Agilent RNA ScreenTape System (Agilent).

A library for RNA sequencing was constructed by using RNA (200 to 500 ng) having RINe of 7 or more by the NEBNext Ultra RNA Library Prep Kit (New England Biolabs) and the nucleotide sequence was determined by HiSeq2000/2500. The data were analyzed by use of the algorithm called as Genomon Fusion (http://genomon.hgc.jp/rna/) publicly disclosed by the human genome analysis center of the Institute of Medical Science, the University of Tokyo. In this manner, fusion genes were identified and expression of the genes was analyzed.

A library of the whole genome sequence was constructed by using WGS using NEBNext DNA Library Prep Reagent (New England Biolabs) and nucleotide sequences were determined by HiSeq2000/2500.

Analysis was carried out as described in TOTOKI Y. et al., NATURE GENETICS 46, 1267-1273 (2014) (doi: 10.1038/ng.3126).
(Results)

The results are shown in FIG. 1. A structural abnormality (fusion gene) in 9p24.1 region was observed in 11 cases out of 57 cases of ATL patients.

A wide variety of structural abnormalities were found as follows: tandem duplication (bold diagonal line from the upper right to the lower left): three cases; inversion (thin diagonal line from the upper left to the lower right): three cases; translocation (open): three cases; and deletion (thin-line from the upper right to the lower left): two cases.

However, all these cases commonly had a deletion of 3'UTR (untranslated region responsible for post transcriptional regulation).

CD274 was intact up to exon 5 in all cases; however, a part of the region on and downstream exon 5 was truncated in some cases.

2. Analysis on the Relationship Between Structural Abnormality of RNAseq (57 Cases) and CD274 Expression
(Method)

The relationship between structural abnormality and CD274 expression was analyzed based on the results of RNA sequencing using ATL (57 cases) tumor specimens of Example 1.

As an expression value, FPKM (Fragments Per Kilobase of transcript per Million fragments sequenced) was used.
(Results)

Figure 2:
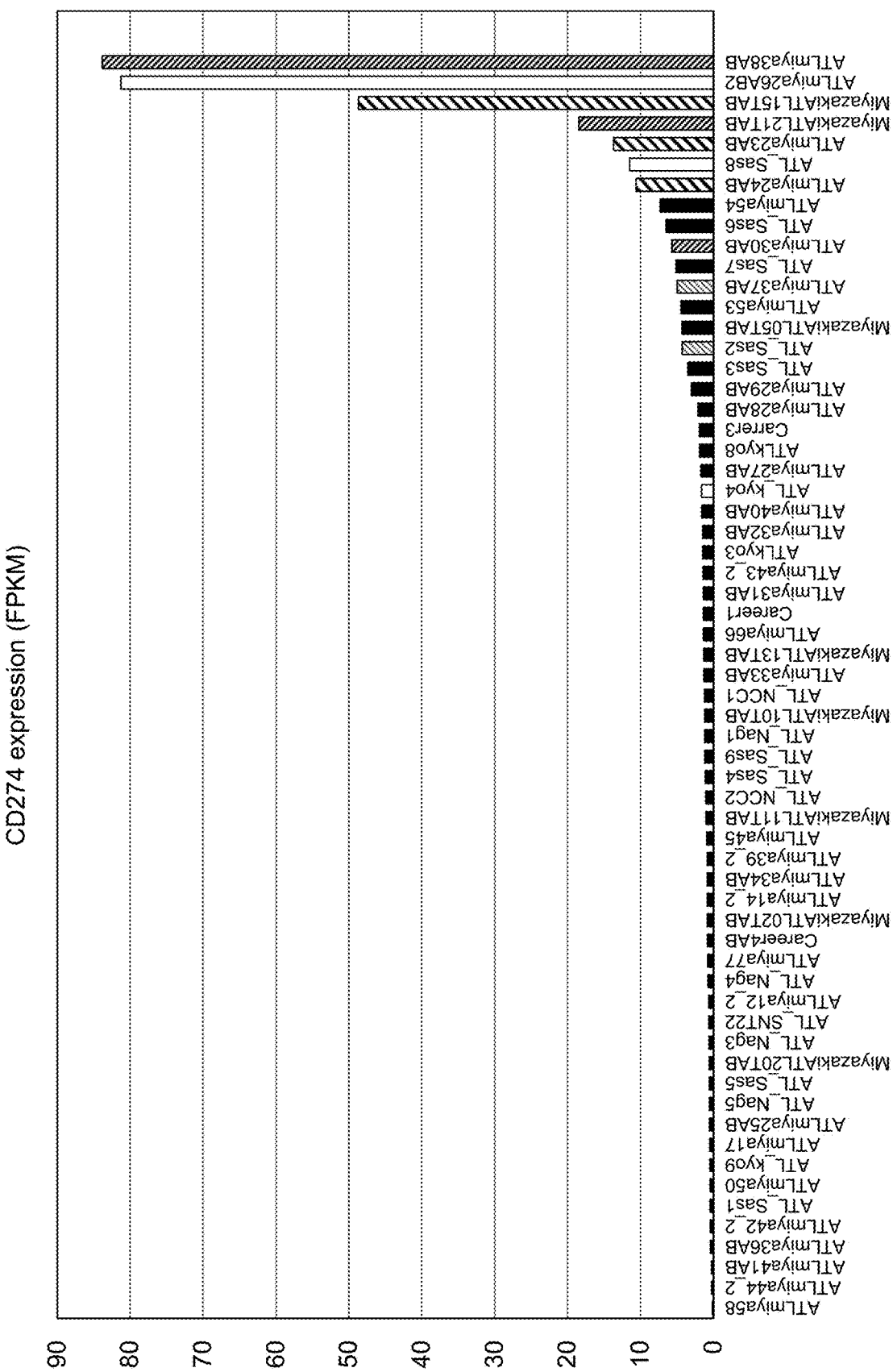
FIG. 2 shows the analysis results on the relationship between structural abnormalities of RNA sequencing (57 cases) and CD274 expression.

The results are shown in FIG. 2. The patterns in the bar graph of FIG. 2 (bold diagonal line from the upper right to the lower left, thin diagonal line from the upper left to the lower right, open, thin-line from the upper right to the lower left) correspond to the patterns of FIG. 1.

In the cases having a structural abnormality (common in Example 1), high expression of CD274 was observed.

CD274 is remarkably and highly expressed in almost all cases having a structural abnormality (+), compared to the cases (solid) having no structural abnormality.

3. Analysis on Expression in Individual Exons of CD274
(Method)

Using RNA sequencing data of ATL (57 cases) in Example 2, the sequence reads were displayed at individual exons of CD274 (NM_014143) by IGV (integrative genome viewer) (provided by Broad Institute).

CD274 consists of 7 exons and exon 7 is mostly occupied by 3'UTR.
(Results)

Figure 3:
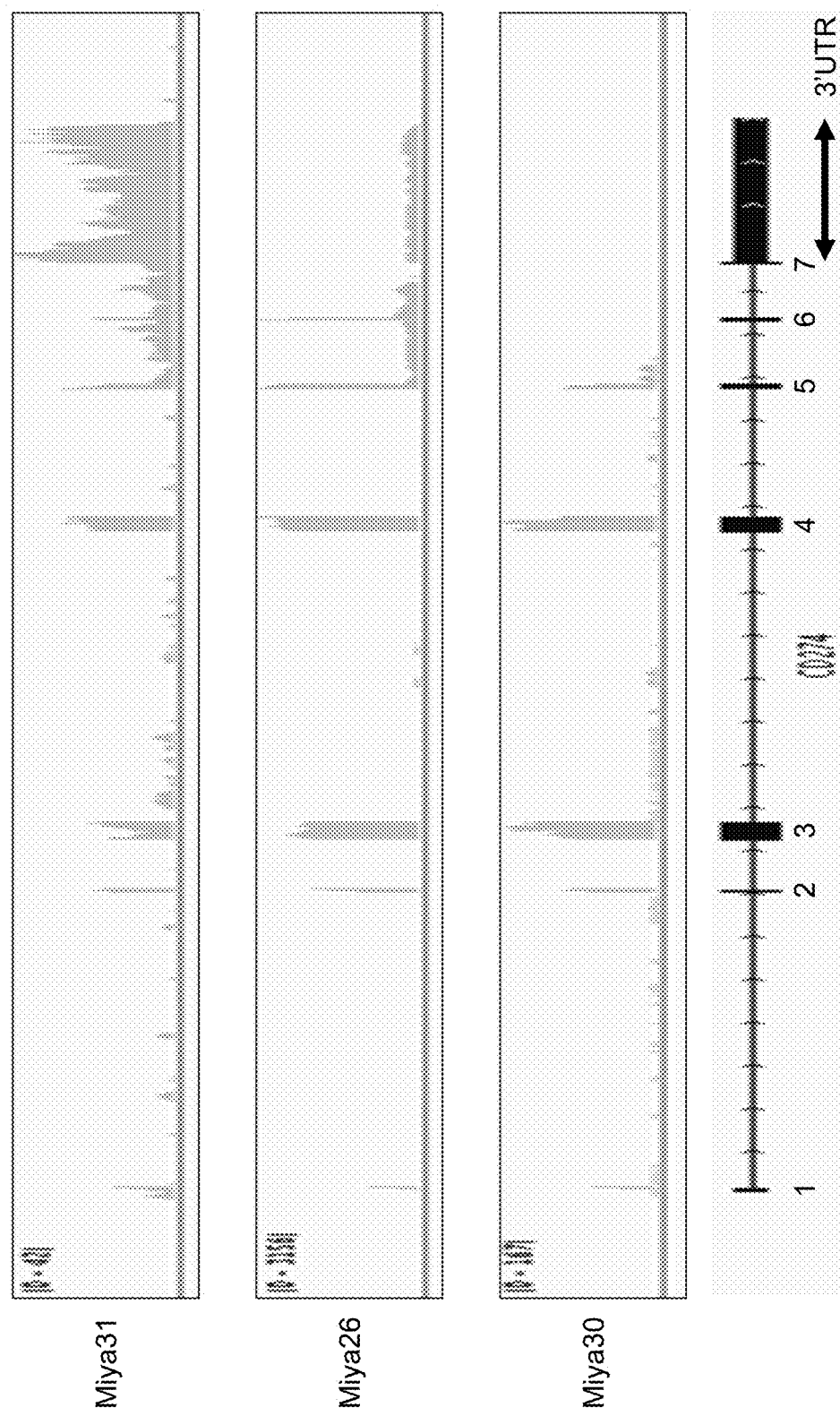
FIG. 3 shows the analysis results of CD274 expression in individual exons.

The results are shown in FIG. 3. The numbers of 1 to 7 in the lower part of FIG. 3 represent the exon numbers. In the case having no structural abnormality (−) (Miya31), expression in 3'UTR was relatively high compared to those of other exons. In contrast, in the cases having a structural abnormality (+) (Miya26 & 30), expression in 3'UTR disappeared. The same results were obtained in other cases of a structural abnormality (+). The results show that in the cases having a structural abnormality (+), expression of the 3'UTR site disappears with deletion of 3'UTR.

4. Expression in Exon 3, and Relationship Between the Ratio of Expression in Exon 3 and Expression in 3'UTR and CD274 Structural Abnormality
(Method)

In the cases having a structural abnormality (+), expression in 3'UTR disappears. Thus, expression is underestimated when expression of the whole gene is evaluated as is in Example 3. As a result, the relationship with structural abnormality likely to be unclear. Then, using RNA sequencing data of ATL (57 cases) of Example 3, the ratios of expression of individual exons of CD274 and expression of 3'UTR were calculated. Of the calculation results, expression of exon 3, which had the most clear relationship with structural abnormality, and the ratio of exon 3 expression/3'UTR expression (ex3 exp/3'UTR exp) was displayed as a scatter chart.
(Results)

Figure 4:
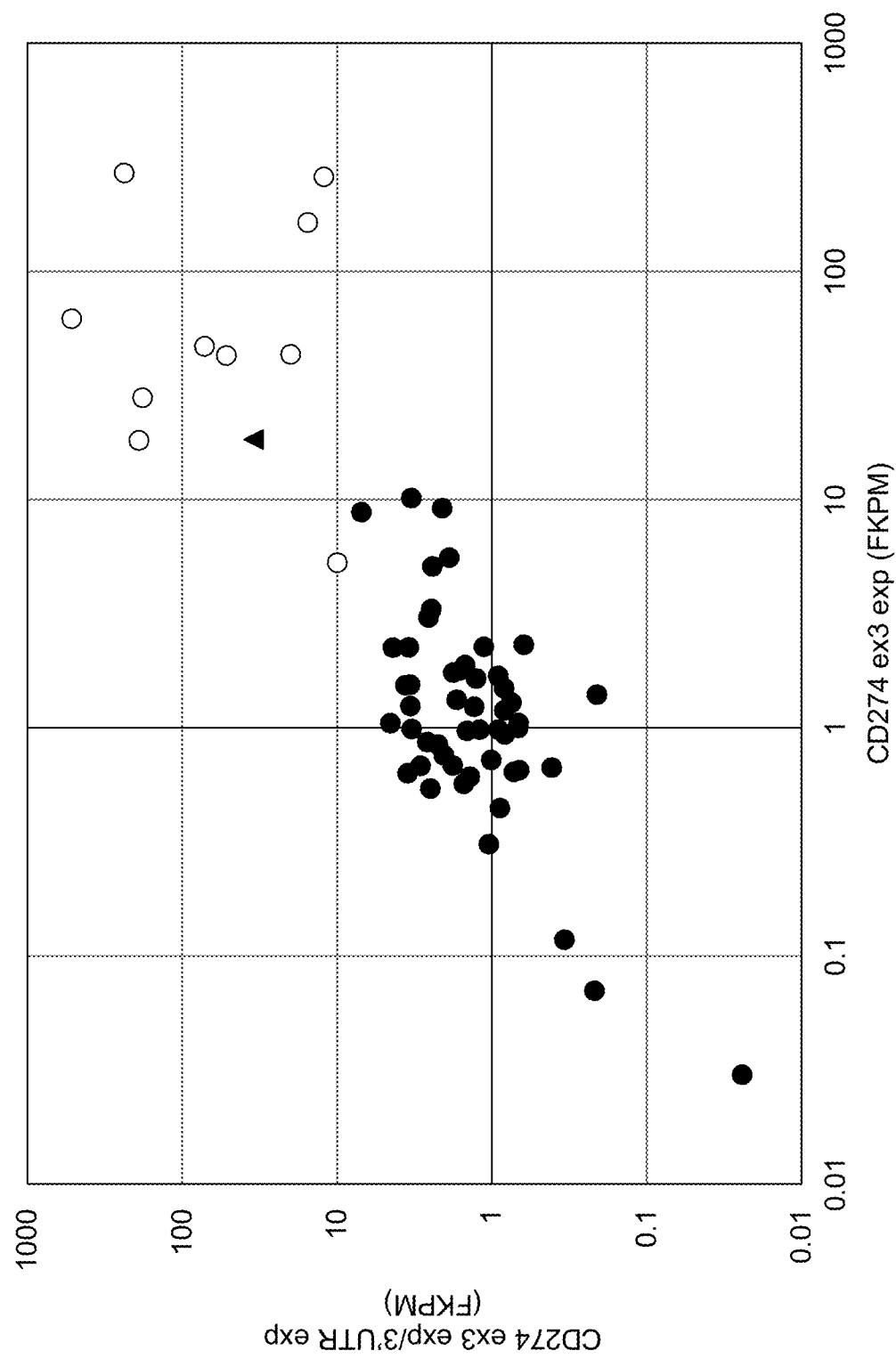
FIG. 4 shows the relationship between expression in exon 3, the ratio of expression in exon 3/3'UTR expression and CD274 structural abnormality.

The results are shown in FIG. 4. In FIG. 4, open circles represent cases having a structural abnormality (+), whereas solid circles represent cases having no structural abnormality (−). The abbreviation "ex3" represents exon 3 and "exp" represents expression. In view of expression of CD274 exon 3 alone and the ratio of exon 3 expression to 3'UTR expression, the ex3 exp/3'UTR exp, is high in structural abnormality (+) cases. Thus, structural abnormality (+) cases (open circle) were clearly separated.

5. Analysis of a Transcript Truncated in the Middle of CD274 Identified in ATL
(Method)

In about half of CD274 structural abnormality (+) cases (11 cases) identified based on RNA sequencing results of ATL cases (57 cases), transcripts were truncated at exon 5 or exon 6. In these cases, the sequences of the transcripts were confirmed by RNA sequencing to identify the sequences.
(Results)

Figure 5:
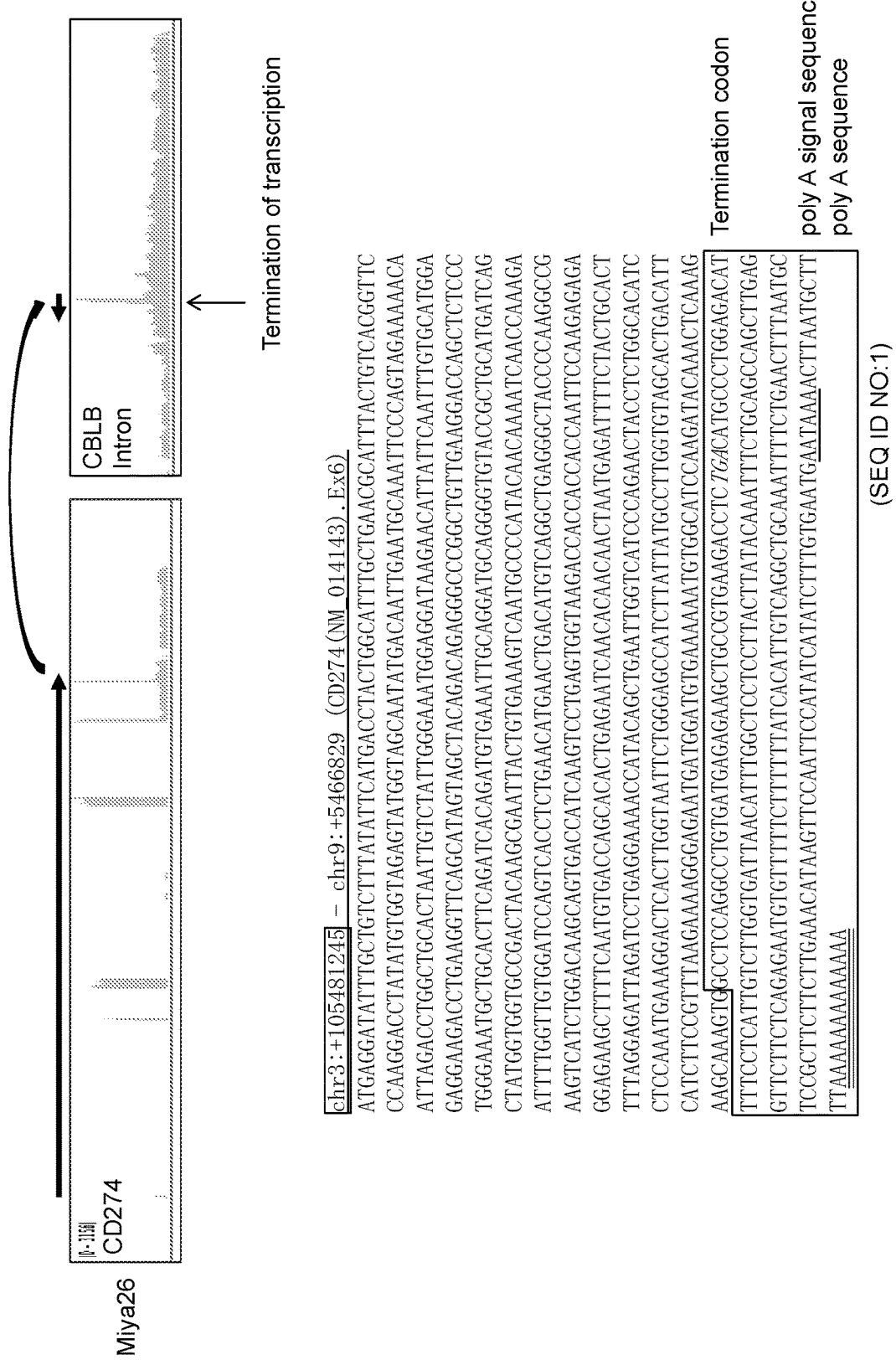
FIG. 5 shows the analysis results of a transcript of CD274 truncated in the middle and identified in ATL.

The results are shown in FIG. 5. The nucleotide sequence in the lower part of FIG. 5 is the sequence of a transcript of a case having a structural abnormality (+) (Miya26). A wild type CD274 was transcribed up to the 3' end of exon 6. The transcript was followed by an intron region of CBLB gene on chromosome 3 (area in the framed). The intron region contains a termination codon (represented by italic TGA), a polyA signal sequence (AATAAA underlined: the sequence required for binding of polyA) and a polyA sequence (double underlined). This result shows that an alternative transcript formed by CD274 structural abnormality functions as a suitable transcript. The whole sequence shown in FIG. 5 is represented by SEQ ID No: 1; whereas the sequence of 3'UTR is represented by SEQ ID No: 2.

6. Amino Acid Sequence of the Case where CD274 Transcript is Truncated in the Middle (Method)

NP_054862 was used as a reference sequence. Based on the sequence of the transcript of Example 5, the amino acid sequence of a case where CD274 was truncated in the middle was identified in silico.

(Results)

Figure 6:
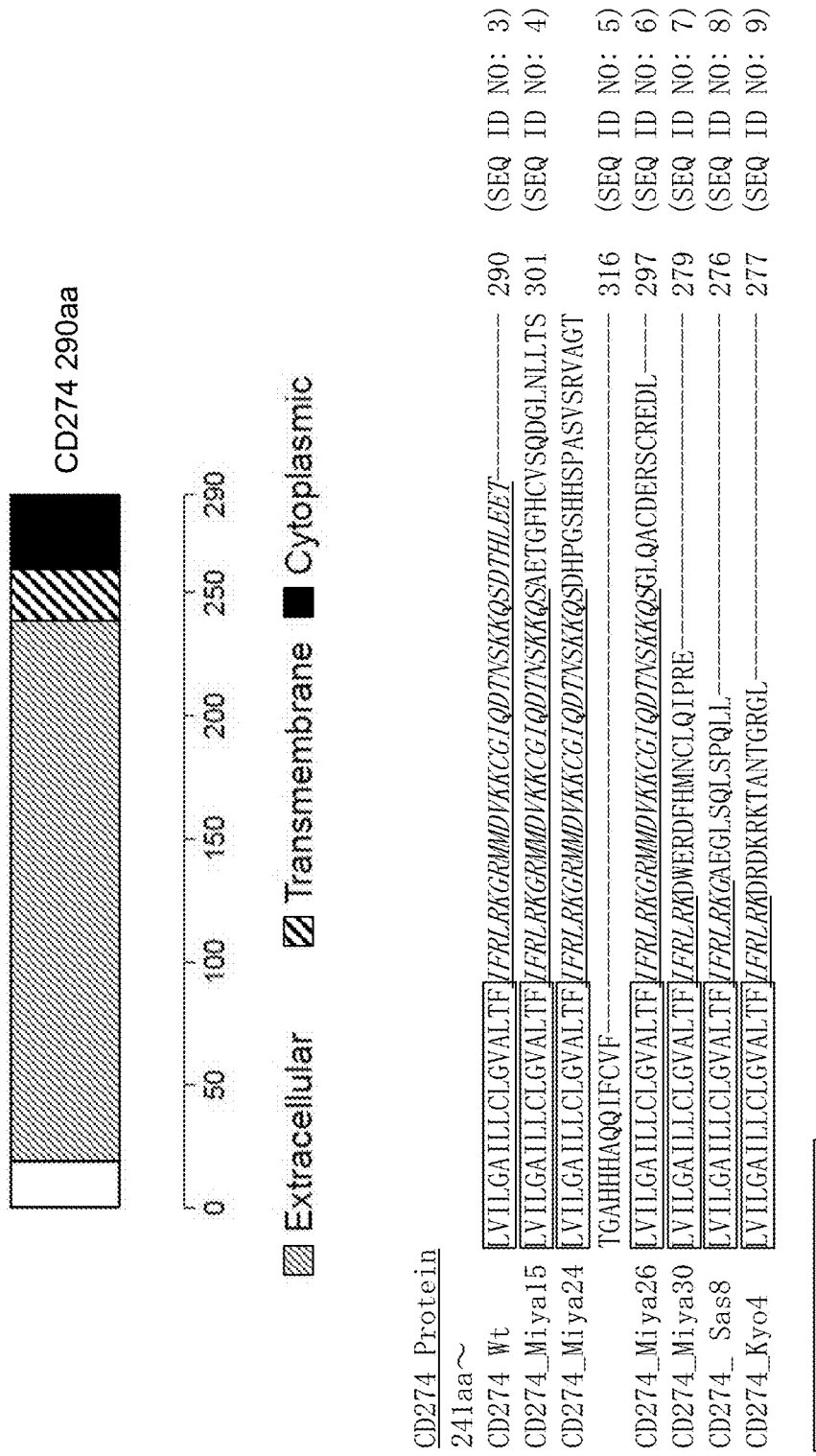
FIG. 6 shows amino acid sequences of transcripts of CD274 truncated in the middle.

The results are shown in FIG. 6. CD274 consists of an Extracellular domain, a Transmembrane domain and a Cytoplasmic domain. The first two domains are considered as important for immune escape of tumor cells due to PD1/PD-L1 mechanism.

In FIG. 6, the sequences from the middle part of transmembrane domains (sequences in frame) are shown. The sequences in the frames are the sequences of transmembrane domains and the sequences italicized and underlined represent the sequences of the cytoplasmic domains. The "CD274 Wt" in the upper part of FIG. 6 represents a wild type sequence.

In the truncated CD274 (Miya15, Miya24, Miya26, Miya30, Sas8, Kyo4), the first two domains are maintained intact, suggesting that the alternative transcripts can function as CD274 with a high probability.

7. Expression of CD274 Protein Evaluated on Membrane Surface of ATL Patient-derived Cell (Method)

CD274 expression on the cell surface was evaluated by flow cytometry using tumor cells in the case where a CD274 structural abnormality was identified by RNA sequencing. Tumor cells were stained with PE/Cy7 anti-human CD274 (B7-H1, PD-L1) Antibody (clone: 29E.2A3, BioLegend) and analyzed by LSR2 Fortessa (BD Biosciences).

(Results)

Figure 7:
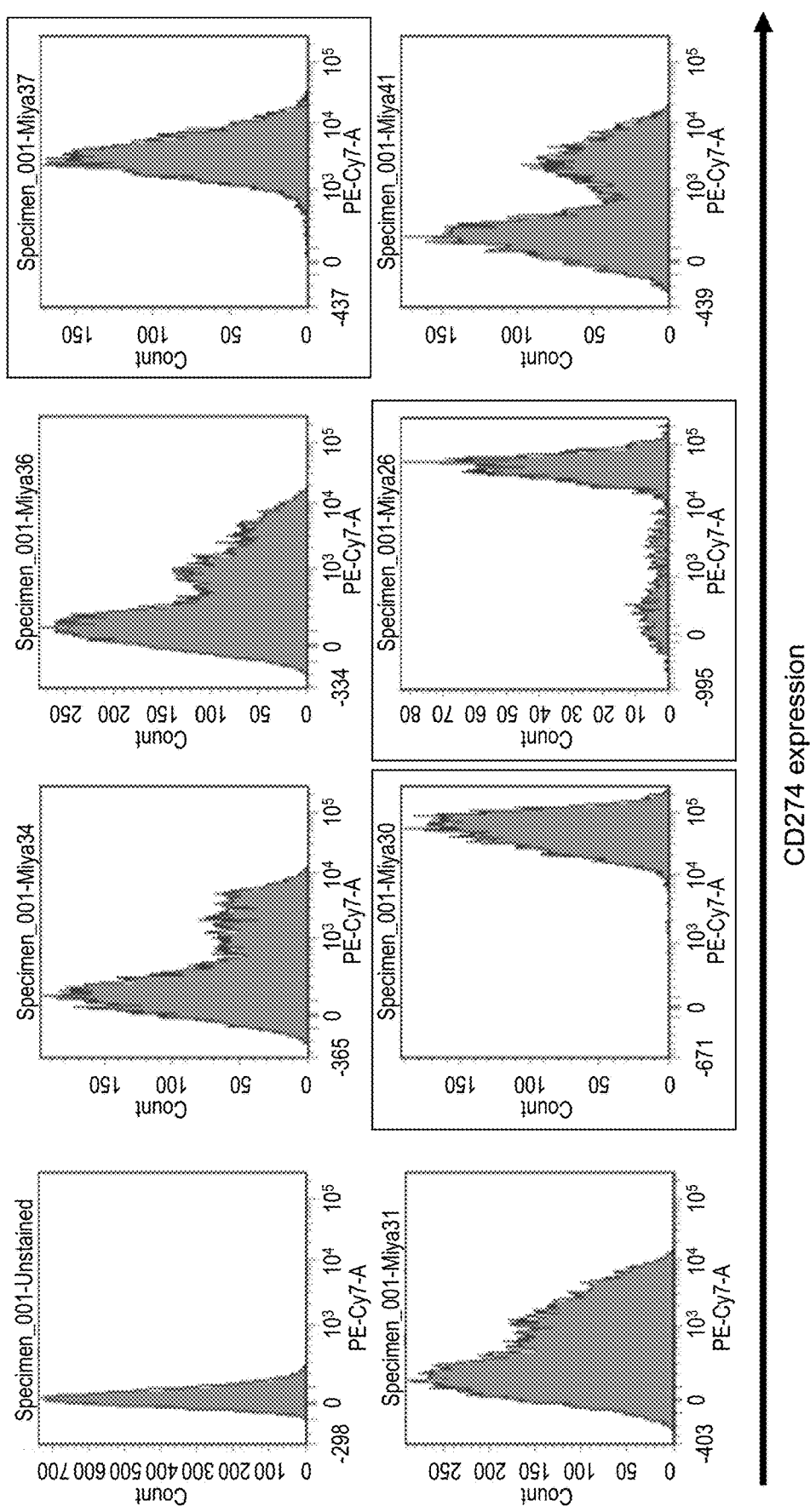
FIG. 7 shows expression of CD274 protein on membrane surfaces of ATL patient-derived cells.

The results are shown in FIG. 7. In FIG. 7, the cases having a structural abnormality (+) each are surrounded by a frame. Also in the cases having a structural abnormality (−), low expression of CD274 is observed; however, in the case having a structural abnormality (+), a significantly high expression of CD274 is confirmed. The expression level was increased about 100 times.

The results show that CD274 is highly expressed at a protein level in the cases having a structural abnormality (+).

8. Analysis of CD274 Structural Abnormality in Various Types of Malignant Tumors Based on TCGA Data and Expression (Method)

Using RNA sequencing data stored in the U.S. database of next generation sequence data of various types of malignant tumors, TCGA (https://tcga-data.nci.nih.gov/tcga/), CD274 structural abnormalities in various types of malignant tumors and expression were analyzed.

(Results)

The results are shown in FIG. 8. In the figure, abbreviations show the following carcinomas. ACC: adenoid cystic carcinoma, BLCA: bladder carcinoma, CESC: cervical squamous cell carcinoma, COAD: colon adenocarcinoma, DLBC: diffuse large B-cell lymphoma, ESCA: esophageal carcinoma, GBM: glioblastoma, HNSC: head-neck squamous cell carcinoma, KICH: kidney chromophobe carcinoma, KIRC: stomach clear cell carcinoma, KIRP: kidney renal papillary cell carcinoma, LAML: acute myelogenous leukemia, LGG: low grade glioma, LIHC: liver hepatocellular carcinoma, LUAD: lung adenocarcinoma, LUSC: lung squamous cellular carcinoma, MESO: malignant mesothelioma, OV: ovarian cancer, PAAD: pancreas adenocarcinoma, PCPG: pheochromocytoma and paraganglioma, PRAD: prostate adenocarcinoma, READ: rectal adenocarcinoma, SARC: sarcoma, SKCM: skin cutaneous melanoma, STAD: stomach adenocarcinoma, TGCT: testicular germ cell tumor, THCA: thyroid carcinoma, THYM: thymoma, UCEC: uterine corpus endometrial carcinoma, UCS: uterine carcinosarcoma, UVM: uveal melanoma (Ctrl: Control)

The numbers in the figure represent the number of specimens of individual tumors subjected to RNA sequencing. In total, 10,000 cases or more were analyzed.

9. CD274 Expression in Individual Cancers (Method)

TCGA publicly discloses expression data (RSEM values are employed and RPKM values are employed only in stomach cancer) calculated based on RNA sequencing data. CD274 expression levels (after logarithmic transformation) of individual cancer cases obtained based on the data were displayed as a histogram.

(Results)

Figure 9:
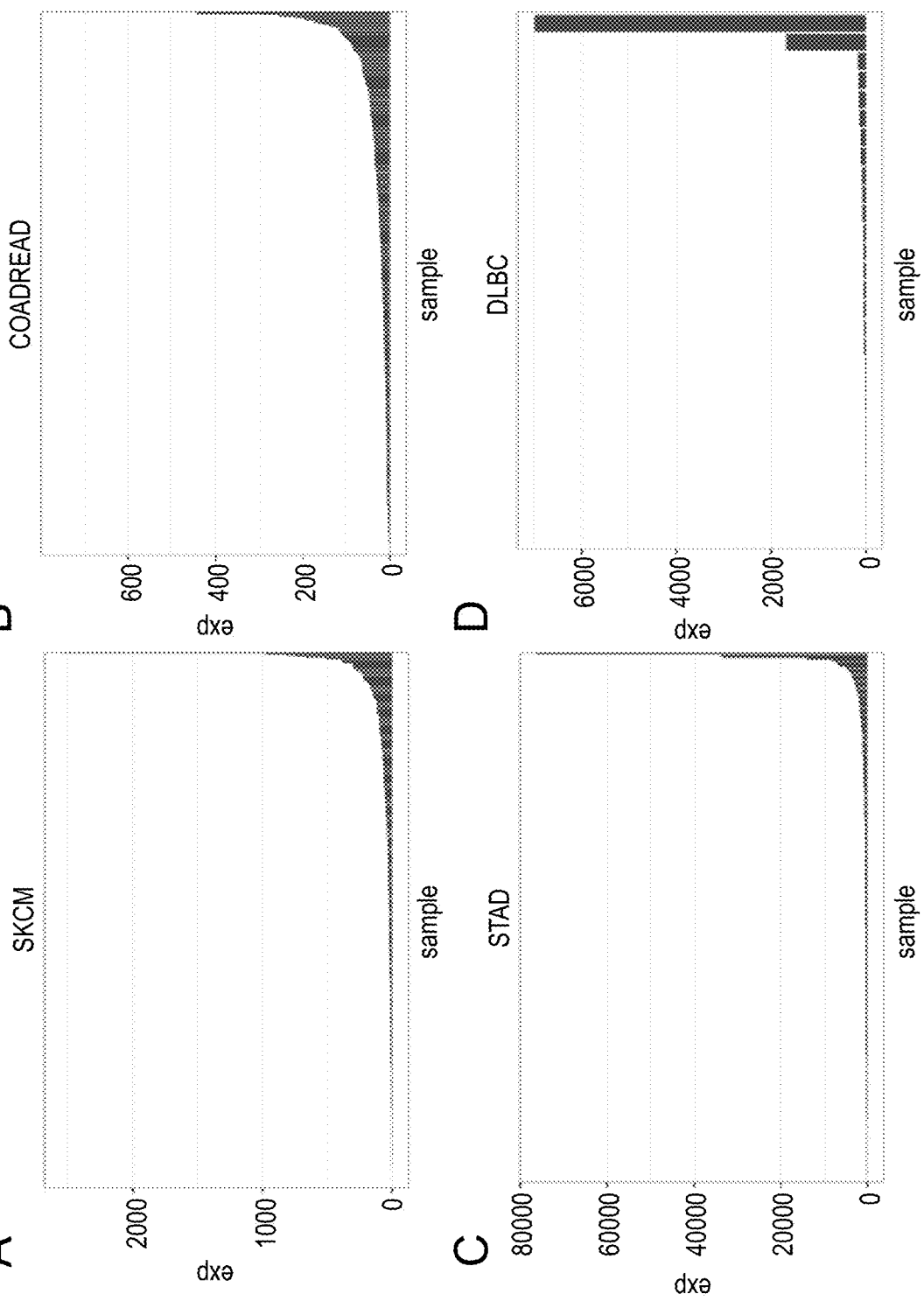
FIG. 9 shows CD274 expression in malignant melanoma, large intestinal cancer, stomach cancer and B cell lymphoma.

FIG. 9 shows the results of four types of cancers. High expression of CD274 was observed in some cases of various cancers. Thus, a cutoff value was determined based on expression values and more specific analysis was performed. As the cutoff value, a logarithmically transformed RSEM values were used in the cases except stomach cancer; whereas a logarithmically transformed RPKM value was used in the case of stomach cancer; more specifically, 8 was used in cancer cases except stomach cancer and 11 was used in the case of stomach cancer (the cutoff values are appropriately set for evaluation). In FIG. 9, SKCM represents skin cutaneous melanoma (FIG. 9A), COADREAD colorectal adenocarcinoma, (FIG. 9B), STAD stomach adenocarcinoma (FIG. 9C) and DLBC diffuse large B-cell lymphoma (FIG. 9D).

10. Analysis of CD274 Expression Based on TCGA Data (Method)

With respect to the cases exhibiting a TCGA cutoff value or more (high CD274 expression case), expressions of individual exons were evaluated based on the RNA sequencing data already mapped, in the same manner as in Example 4, and displayed by the IGV (integrative genome viewer) (provided by Broad Institute).

(Results)

The results are shown in FIG. 10. Of the cases there, cases of showing the same expression pattern as ATL (high expression and no 3'UTR expression) were found. Further, in these cases, the sequences were more specifically analyzed based on RNA sequencing data. As a result, a structural abnormality of CD274 was confirmed. For example, stomach adenocarcinoma (STAD) (FIG. 10A) and colon adenocarcinoma (COAD) (FIG. 10B) are mentioned. Other than these, bladder carcinoma (BLCA): single case; cervical squamous cell carcinoma (CESC): single case; kidney renal clear cell carcinoma (KIRC): single case; lung adenocarcinoma (LUAD): two cases; colon adenocarcinoma (COAD): single case (two cases in total)/rectal cancer (READ): single case; cutaneous malignant melanoma (SKCM): single case; and stomach adenocarcinoma (STAD): three cases (4 cases in total) were the cases where the same expression pattern as ATL (high CD274 expression and no 3'UTR expression) was found.

Figure 11:
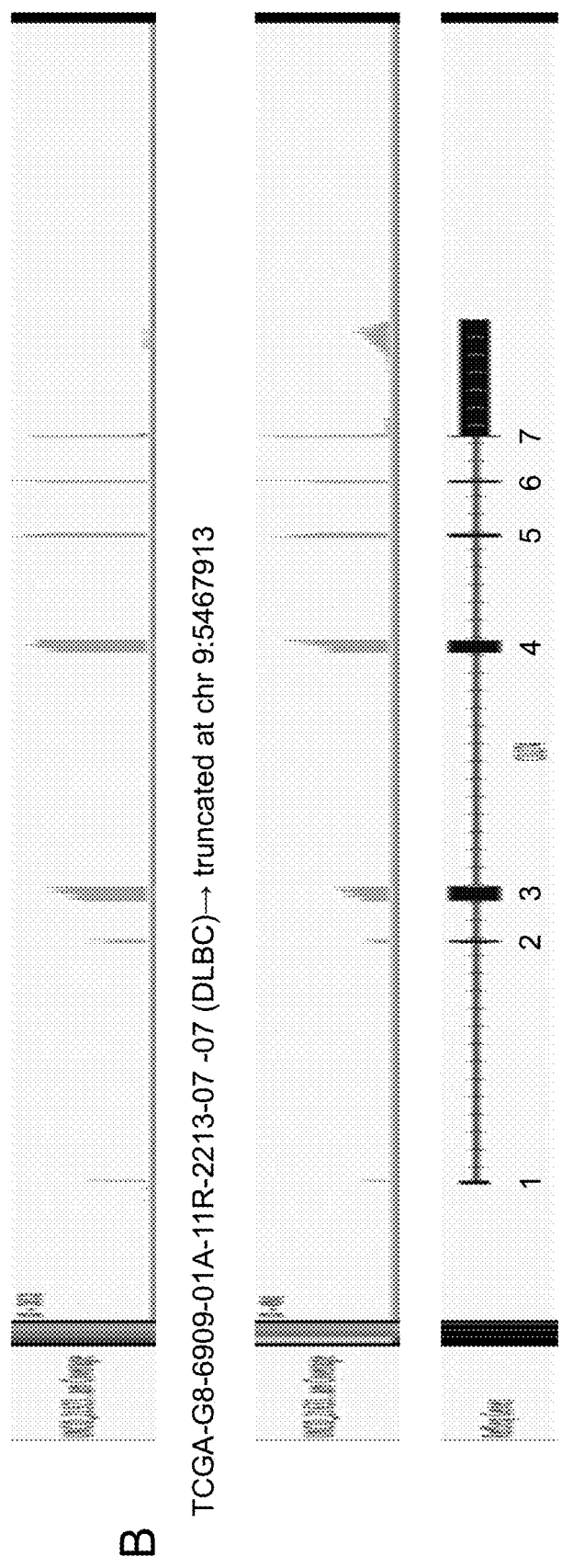
FIG. 11 shows analysis results (II) of CD274 expression in various types of malignant tumors based on TCGA data.

In FIG. 11, two cases of diffuse large B-cell lymphoma (DLBC) were similarly shown as an example (FIGS. 11A and B). In DLBC, CD274 was highly expressed in 2 cases out of 48 cases having RNA sequencing data and the same structural abnormality was found in both of the two cases.

Numbers 1 to 7 in the lower parts of FIGS. 10 and 11 represent exon numbers.

The results shown in FIGS. 10 and 11 demonstrate that structural abnormality of CD274 including 3'UTR and high expression of CD274 in association with the structural abnormality occur in various types of cancers.

11. Detection of CD274 Abnormality Using SNP Array
(Method)

Copy number analysis was performed by SNP array (method: GISTIC) in ATL 426 cases.

From patients who were diagnosed as ATL and their informed consents were obtained, tumor specimens were taken in accordance with the protocol approved by the ethical committee of Kyoto University and subjected to global genetic mutation analysis.

First, copy number analysis using tumor specimens of ATL 426 cases was carried out by SNP array (Affymetrix 250K 282 cases, Illumina 610K 144 cases). As the algorithm, CNAG/AsCNAR and GISTIC2.0 were used. An increase or decrease in number of copies at local sites was identified.
(Results)

Figure 12:
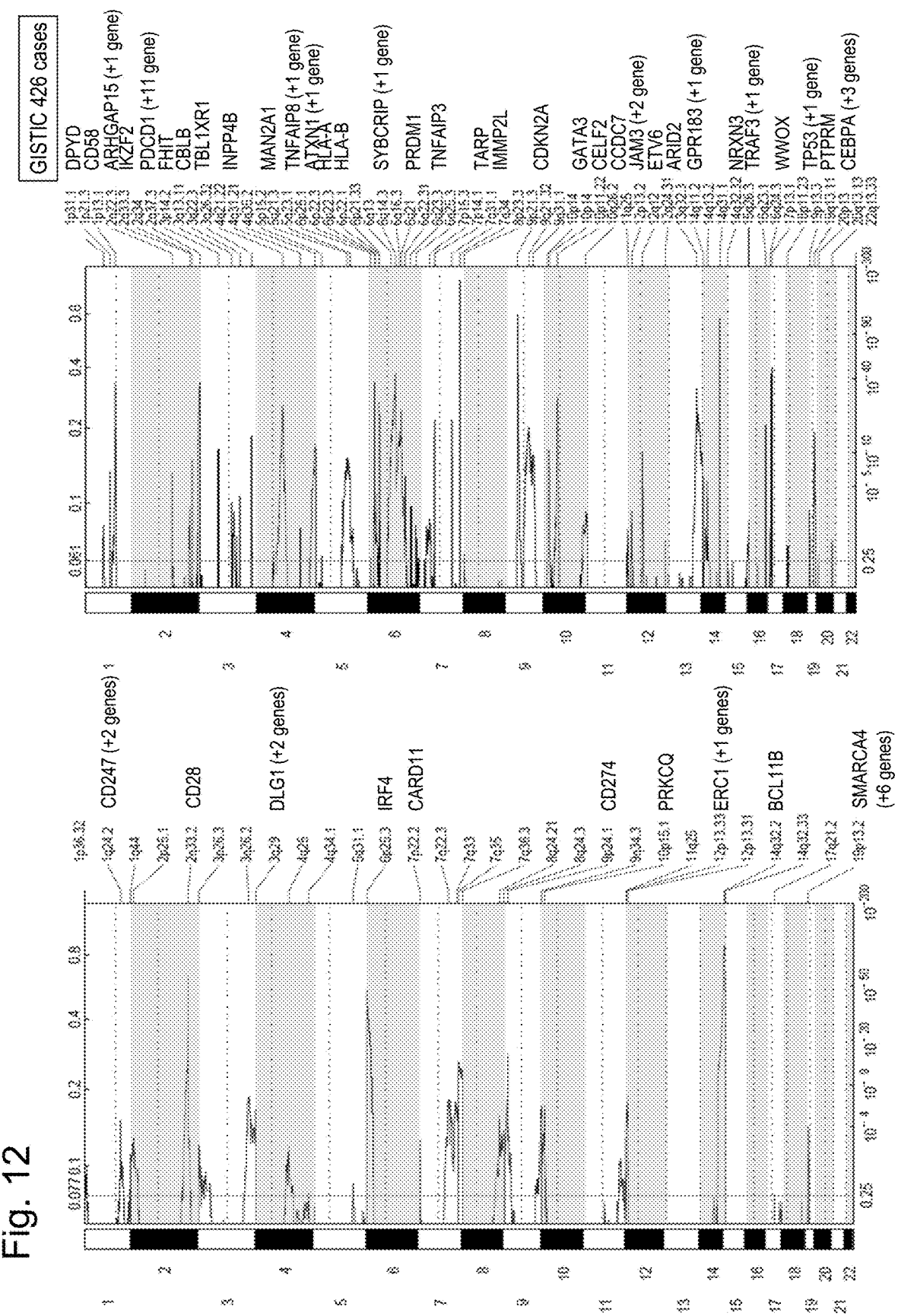
FIG. 12 shows results (GISTIC results) of CD274 abnormalities detected by SNP array.

The results based on GISTIC are shown in FIG. 12. In the ATL patients, the number of copies increased at 26 local sites and the number of copies decreased at 50 local sites. One of the sites is 9p24.1 region, at which tandem duplication (14%) of CD274 (PD-L1) was observed.

Figure 13:
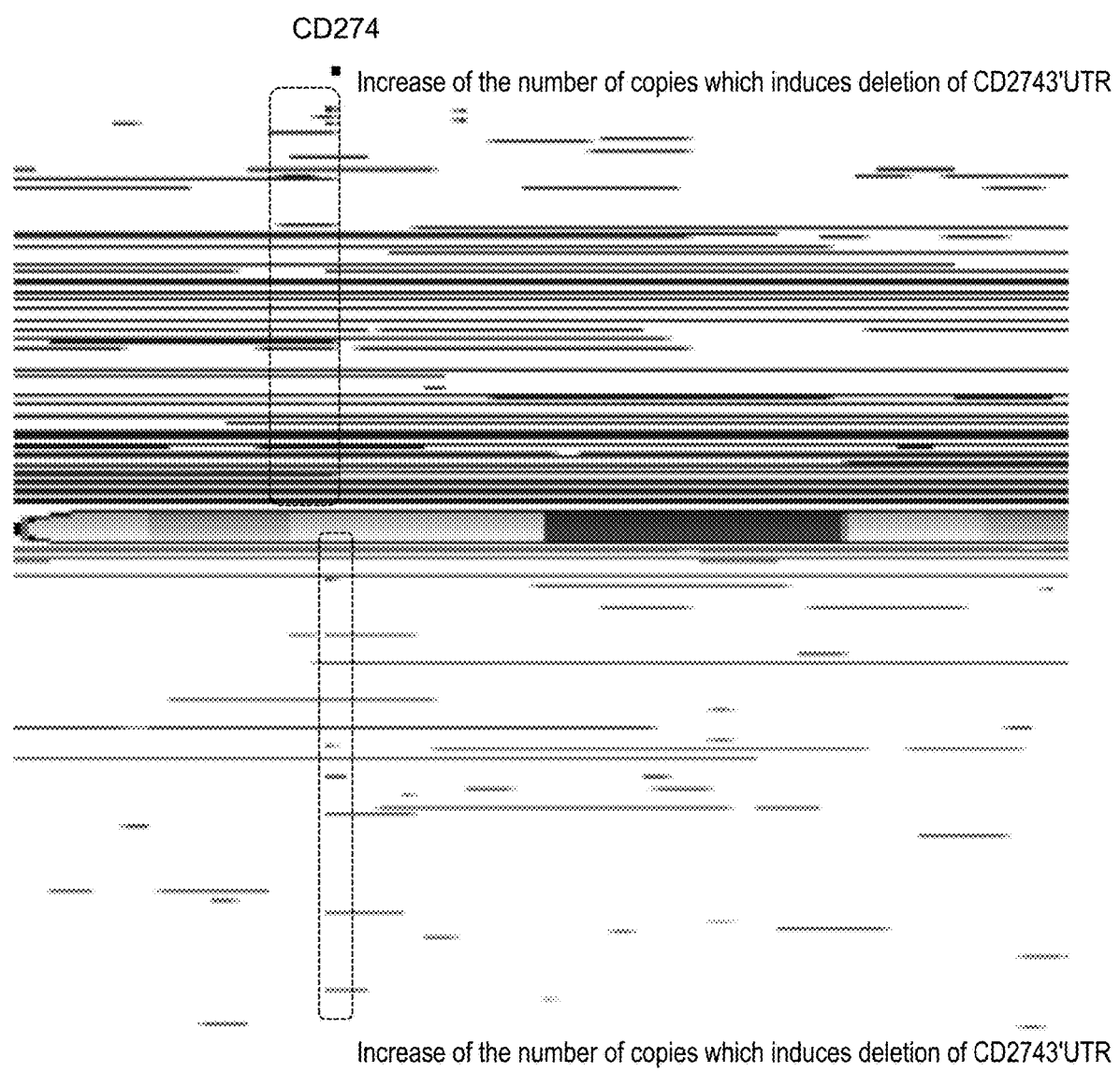
FIG. 13 shows results (CNAG results) of CD274 abnormalities detected by SNP array.

The results based on CNAG are shown in FIG. 13. In FIG. 13, an increase in copy number is shown in the upper panel; whereas a decrease in copy number is shown in the lower panel. Most of the copies tandemly amplified in 9p24.1 region (called in GISTIC) were truncated copies containing CD274 gene up to the middle thereof and lacking 3'UTR. A decrease in number of copies including part of the 3' side of CD274 gene was observed, demonstrating that a defective 3'UTR is also caused by a decrease in copy number. At least, in the cases having an increase in copy number of Miya23, Miya24 and Miya26, a structural abnormality (+) having defective 3'UTR was found by whole genome sequencing and high expression of CD274 was found by RNA sequencing. The same findings were obtained also in the cases having a decrease in copy number of Miya37, Miya38 and Sas2.

12. Detection of CD274 Abnormality by RQ-PCR
(Method)

Expression of CD274 was evaluated by RQ-PCR in 13 ATL cases.

RNA was extracted from ATL tumor specimens by RNeasy Mini kit (QIAGEN) and subjected to reverse transcription by ReverTra Ace (registered trade mark) qPCR RT Kit (TOYOBO), and then, PCR was carried out by SYBR Premix Ex Taq II (TAKARA). The sequence of the forward primer was GGCATCCAAGATACAAACTCAA (SEQ ID NO: 10) and the sequence of the reverse primer was CAGAAGTTCCAATGCTGGATTA (SEQ ID NO: 11). In PCR, a holding step was carried out at 95° C. 10 sec, and a cycling step (95° C. 5 sec, 60° C. 30 sec, 72° C. 30 sec) was repeated 50 times. Detection was carried out by LightCycler (registered trade mark) 480 System (Roche Applied Science). As the internal control, 18S was used and the ratio to CD274 was shown.
(Results)

Figure 14:
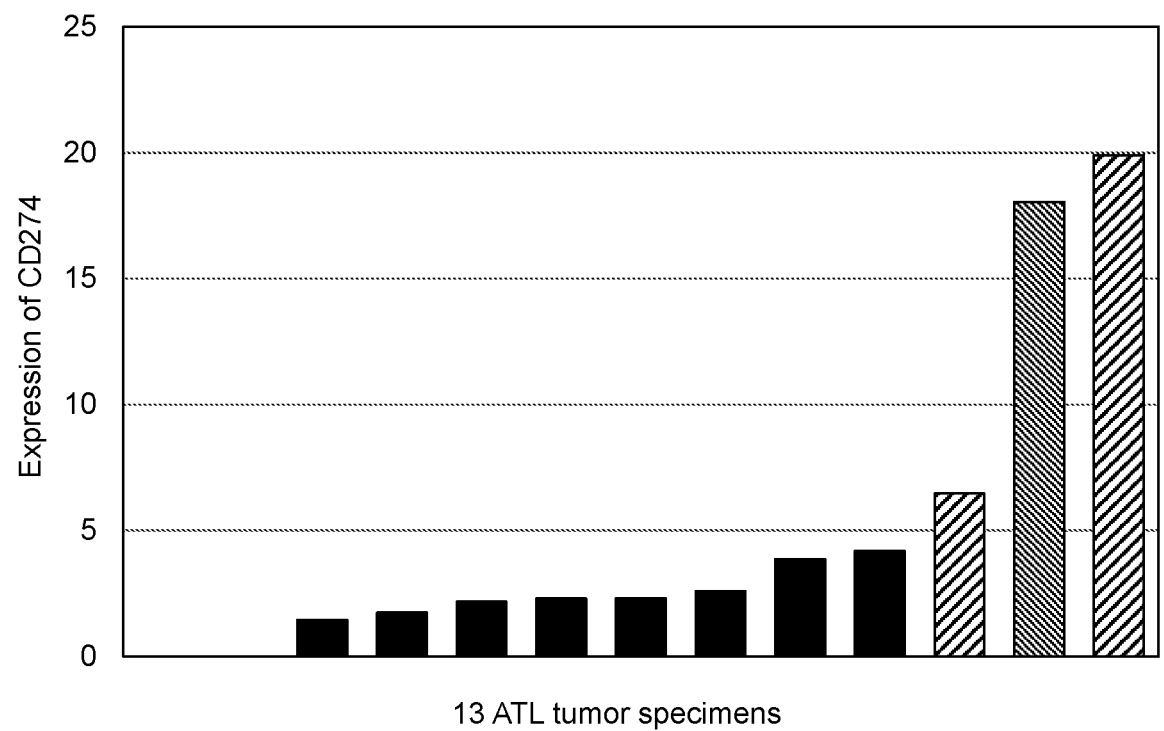
FIG. 14 shows results of CD274 abnormalities detected by RQ-PCR.

The results are shown in FIG. 14. In the cases of ATL patients, three cases having a structural abnormality were observed (in the bar chart, two bars with a bold diagonal line from the upper right to the lower left (tandem duplication was observed) and a single bar with a thin diagonal line from the upper left to the lower right (inversion was observed)). In these cases, CD274 was highly expressed.

13. Immunostaining PD-L1 in ATL
(Method)

In three cases, i.e., ATL059 having no PD-L1 structural abnormality (SV: structural variation), ATL075 of PD-L1 SV (+) having an intact ORF and ATL012 of SV (+) having a truncated ORF, PD-L1 was immuno-stained with an anti N terminal antibody (E1J2J, Cell Signaling Technology) and an anti C terminal antibody (SP142, Spring Bioscience).

An antigen antibody complex was visualized by Histofine (registered trade mark) Simple Stain MAX PO (Nichirei Bioscience).
(Results)

Figure 15:
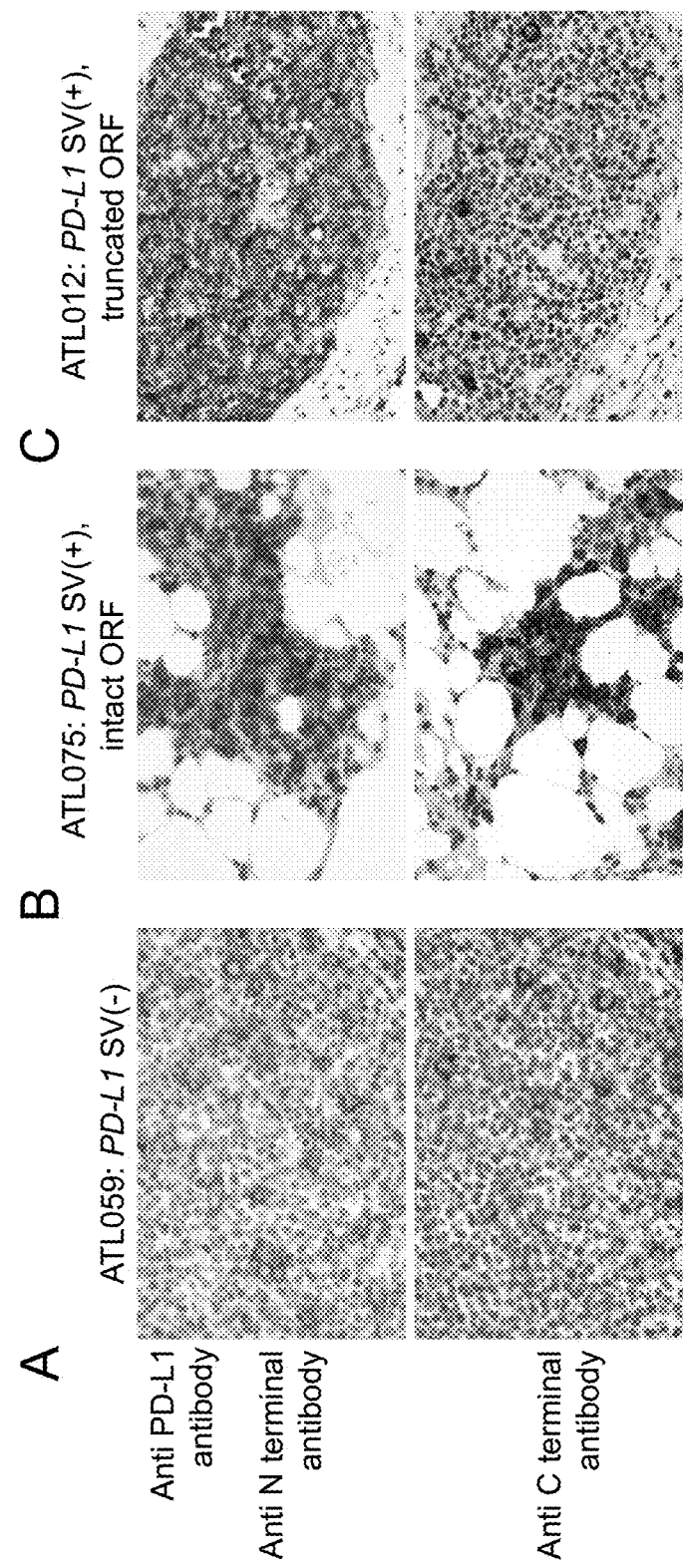
FIG. 15 shows immunostaining results of PD-L1 expression in ATL patients, i.e. ATL059 (FIG. 15A), ATL075 (FIG. 15B) and ATL012 (FIG. 15C).

The results are shown in FIG. 15. FIG. 15A shows the results of ATL059 having no PD-L1 SV (ATL059: PD-L1 SV (−)). FIG. 15B shows the results of ATL075 of PD-L1 SV (+) having an intact ORF (ATL075: PD-L1 SV (+), intact ORF). FIG. 15C shows the results of ATL012 of SV (+) having a truncated ORF (ATL012: PD-L1 SV (+), truncated ORF). In the upper panel of FIG. 15, the results of immunostaining with the anti N terminal antibody are shown. In the lower panel of FIG. 15, the results of immunostaining with the anti C terminal antibody are shown. As shown in FIG. 15A, in ATL059 having no PD-L1 SV, tumor cells were not stained (in FIG. 15A, cells sporadically stained (looks in grey in a monochrome photography) are macrophages).

As shown in FIG. 15B, ATL075 of PD-L1 SV (+) having an intact ORF was intensively stained with both anti N terminal antibody and anti C terminal antibody.

As shown in FIG. 15C, ATL012 of SV (+) having a truncated ORF was intensively stained with the anti N terminal antibody and not stained with the anti C terminal antibody.

The results show that if PD-L1 SV is present, expression of PD-L1 (at a protein level) is strong and increases. The fact that ATL012 is not stained with the anti C terminal antibody is consistent with the fact that ORF is truncated. Further, the results show that PD-L1 SV can be identified by double staining with the anti N terminal antibody and anti C terminal antibody.

The results show that the same results are obtained also in western blot by antibodies against PD-L1, i.e., an anti N terminal antibody and an anti C terminal antibody.

14. Expression of PD-L1 in Various Types of Carcinomas
(Method)

Cases (lowest 30 cases) corresponding to top 10% were selected based on 33 types of carcinomas (solid cancer) publicly disclosed from TCGA and expression data (RSEM values) calculated based on RNA sequencing data of 10210 cases. RNA sequencing data were downloaded, and cases of CD274 fusion gene (+) and/or a virus insert (+) in the CD274 region and/or a relative high CD274 exon 4/3'UTR ratio were selected. As to DLBC and STAD, since a frequency was high, all cases were used as subjects.

RNA sequencing data of total 1691 cases were downloaded and analyzed. Based on the data, expression of CD274 (after RPKM value of exon 4 was logarithmically transformed) of individual cases of each carcinoma was displayed.

(Results)

Figure 16:
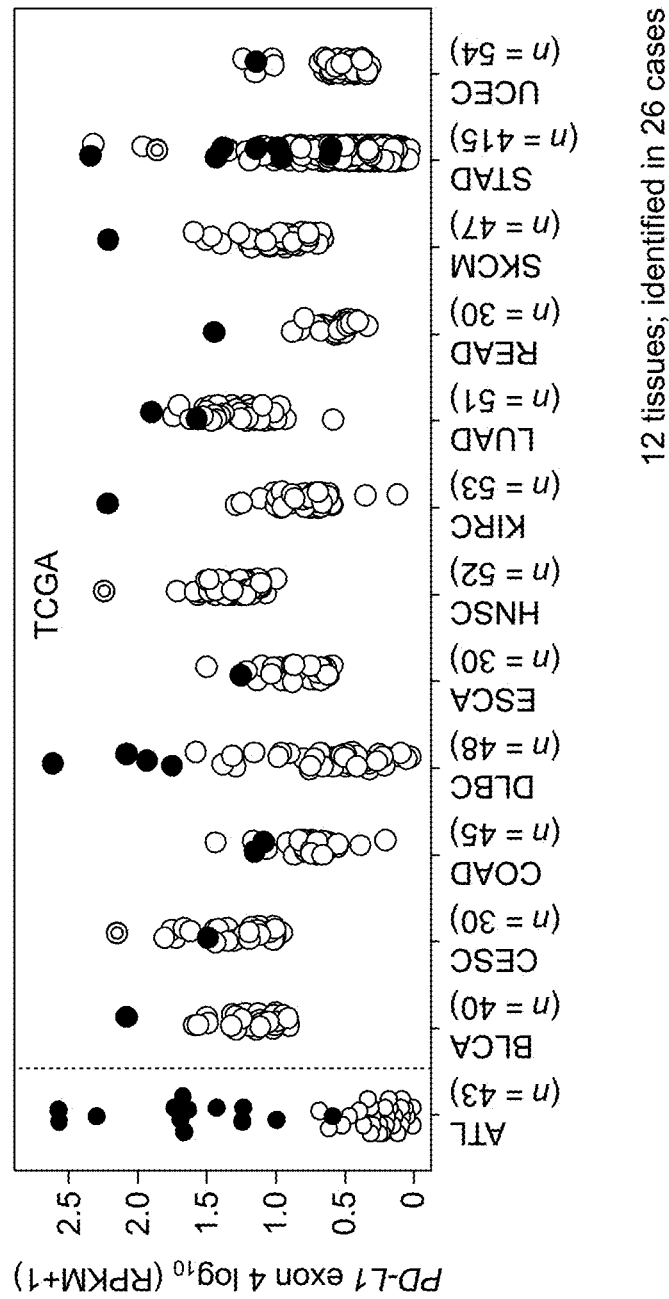
FIG. 16 shows analysis results (II) of CD274 structural abnormality and expression in various types of cancers based on TCGA data.

The results are shown in FIG. 16.

In FIG. 16, solid circles represent cases of CD274 fusion gene (+) and/or a relative high CD274 exon 4/3'UTR ratio. Double circles represent cases having a virus insert (+) in the CD274 region.

In 12 cancer tissues in total (26 cases in total), CD274 fusion gene (+) and/or a virus insert (+) in the CD274 region and/or a relatively high CD274 exon 4/3'UTR ratio were observed. From the results, it was found that an abnormality of truncated 3'UTR in CD274 was observed in various types of cancers. Further, these cases mostly occur where CD274 is most highly expressed in carcinomas, suggesting that 3'UTR is extremely important for regulating CD274 expression.

BLCA: bladder carcinoma: single case
CESC: cervical squamous cell carcinoma: 2 cases
COAD: colon adenocarcinoma: 2 cases
DLBC: diffuse large B-cell lymphoma: 4 cases
ESCA: esophageal carcinoma (: single case
HNSC: head-neck squamous cell carcinoma: single case
KIRC: kidney clear cell carcinoma: single case
LUAD: lung adenocarcinoma: 2 cases
READ: rectal adenocarcinoma: single case
SKCM: skin cutaneous melanoma: single case
STAD: stomach adenocarcinoma: 9 cases
UCEC: uterine corpus endometrial carcinoma: single case 15. Insertion of Carcinogenesis Virus in the CD274 Region and Abnormality of CD274 3'UTR (Method)

Using 1,691-case RNA sequencing data downloaded from TCGA, whether insertion of a cancer-related virus in the genome is found within CD274 gene or the periphery thereof was investigated.

(Results)

Of them, in the 26 cases as mentioned above, three cases (CESC: single case, HNSC: single case, STAD: single case) had an insertion of a carcinogenesis virus in the CD274 region.

Figure 17:
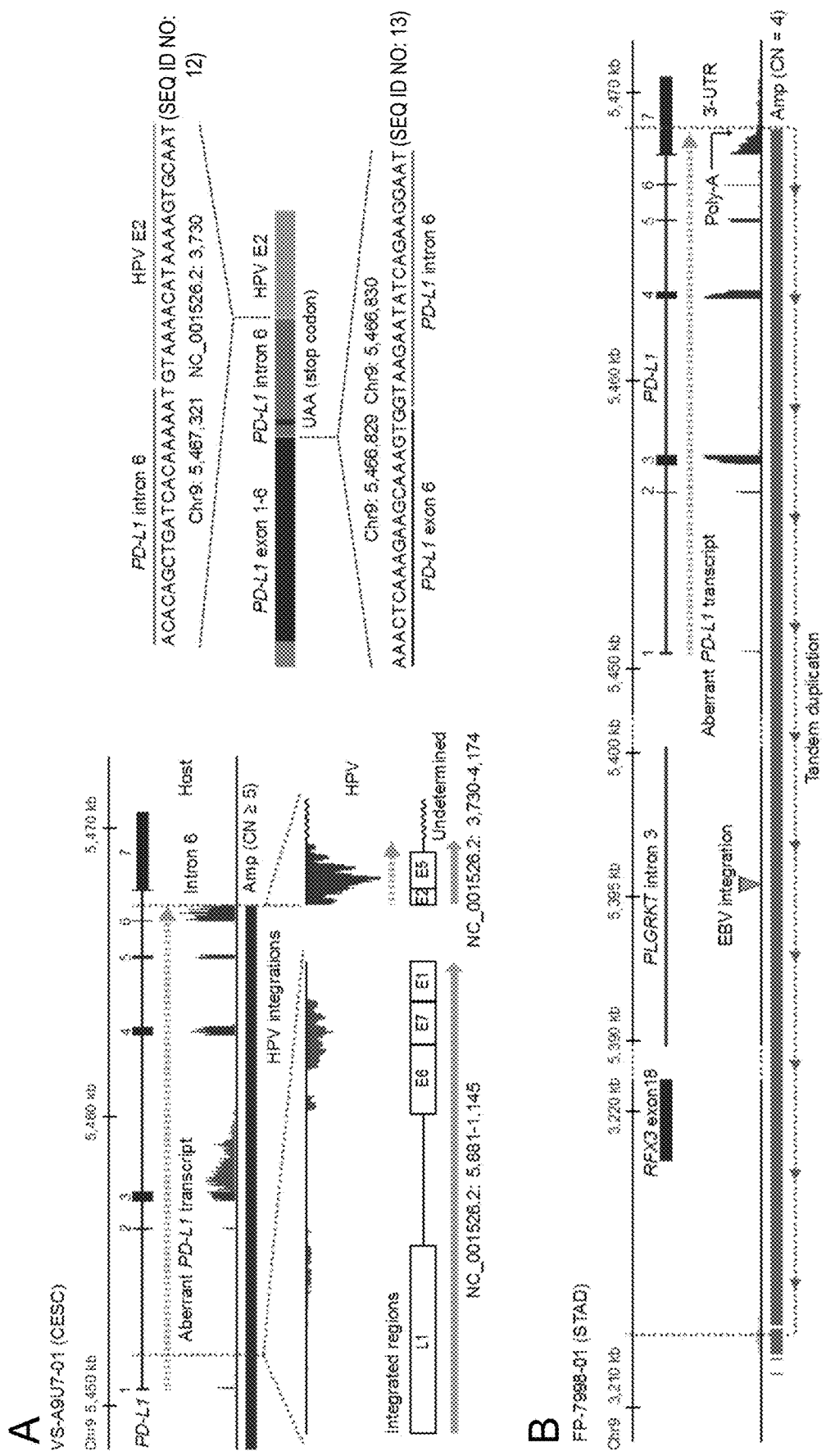
FIG. 17 shows an insert of a carcinogenesis virus in CD274 region and abnormality in CD274 3'UTR.

FIG. 17 shows the verification results of a VS-A9U7-01 case (CESC) (FIG. 17A) and a FP-7998-01 case (STAD) (FIG. 17B).

In the VS-A9U7-01 case (CESC) having an insert of Human papilloma virus (HPV) 16 in intron 6 of CD274, the ORF of a CD274 transcript was truncated in exon 6 and a transcript having CD274 intron 6 followed by HPV (human papilloma virus) E2/E5 gene was formed.

In the FP-7998-01 case (STAD) having an insert of Epstein-Barr virus (EBV) in intron 3 of PLGRKT, which is an upstream gene adjacent to CD274, tandem duplication including the region occurred and a CD274 transcript was truncated at 3'UTR.

These results show that insertion of a carcinogenesis virus in the CD274 region is associated with abnormality of CD274 3'UTR.

16. CD274 Expression is Remarkably Increased by Introducing a Deletion or an Inversion in CD274 3'UTR by CRISPR/Cas9 System.

(Method)

A human (upper panel) or mouse (lower panel) cell line was transfected with sgRNA and Cas9 (targeting two sites: 5' end and 3' end of CD274 3'UTR). In this manner, to these cell lines, a deletion or inversion corresponding to the whole length (2.7 kb) of CD274 3'UTR was introduced by CRISPR (clustered regularly interspaced short palindoromic repeats)/Cas9 system. The resultant cells were purified and CD274 expression on the cell surface was evaluated by flow cytometry. Whether a desired deletion or inversion was introduced was confirmed by PCR and sequencing.

As subjects, human cell lines, i.e., HEK293T (fetal kidney), T2 (hybrid of T cell and B cell), PC-9 (lung cancer) and mouse cell lines, i.e., EG7-OVA (T cell lymphoma, expressing Ovalbumin), P815 (mastocytoma) and B16-F10 (malignant melanoma) were selected.

(Results)

Figure 18:
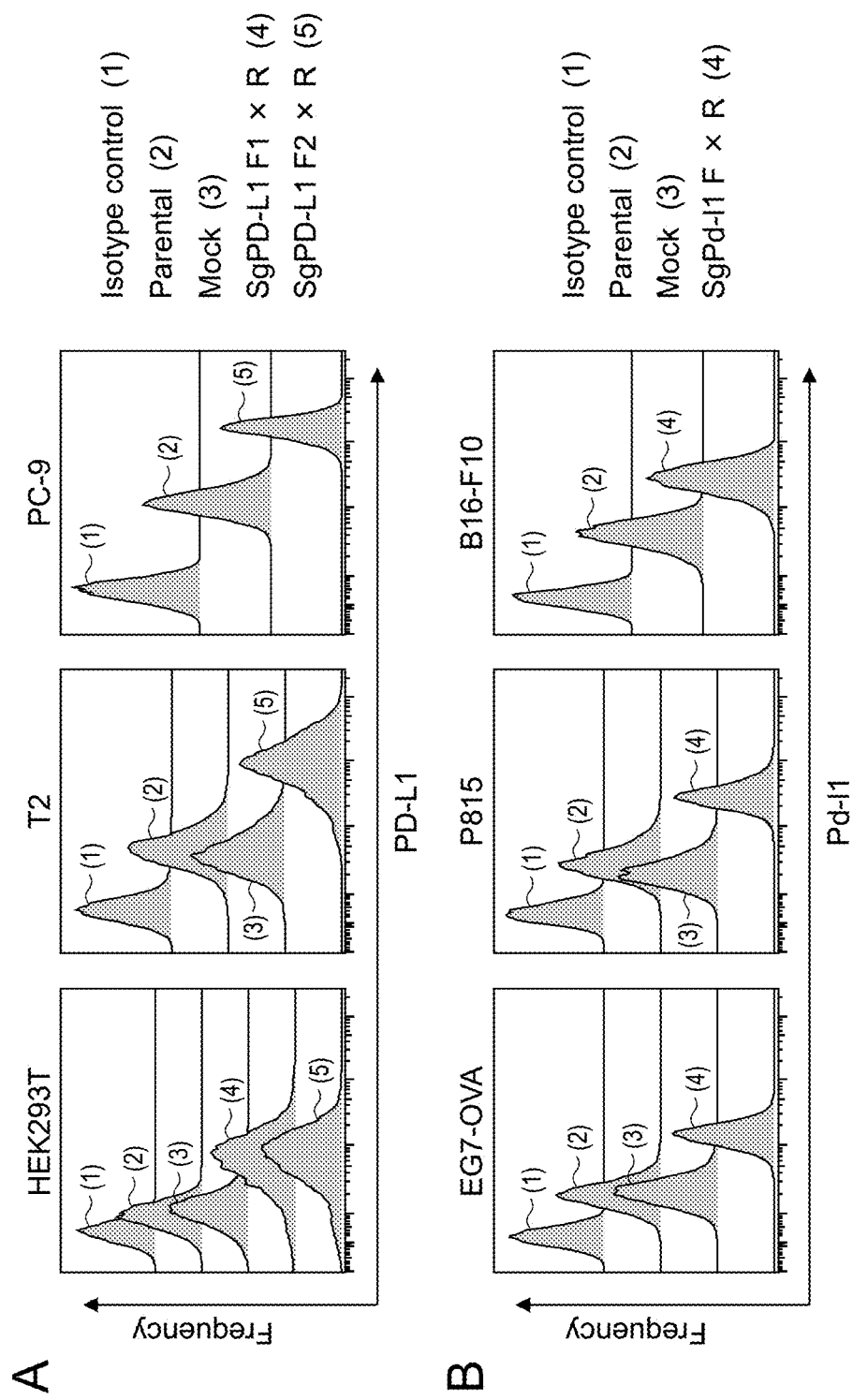
FIG. 18 shows that CD274 overexpression induced by introducing an abnormality of CD274 3'UTR of a human and mouse cell lines. The results of human cell lines are shown in FIG. 18A and the results of mouse cell lines are shown in FIG. 18B.

The results are shown in FIG. 18. The results of human cell lines are shown in the upper panel and the results of mouse cell lines are shown in the lower panel.

As a result, in all human/mouse cell lines used as subjects, the cell lines (SgPD-L1 FxR) having a deletion or an inversion introduced in the 3'UTR exhibited a remarkable increase in CD274 expression, compared to parental cell lines and mock introduced cell lines.

These results experimentally prove that there is a causal relationship between a structural abnormality of CD274 3'UTR identified by gene analysis and high expression of CD274; more specifically that overexpression of CD274 is induced by abnormality of CD274 3'UTR.

17. High Expression of CD274 in Association with CD274 3'UTR Abnormality Induces Apoptosis of PD-1 Expressing T Cells (Method)

To evaluate the effect of high expression of CD274 in association with CD274 3'UTR abnormality on the immunity system in vitro, a PC-9 cell line in which high expression of CD274 in association with CD274 3'UTR abnormality was induced by the CRISPR-Cas9 system or a control cell line (Mock), and Jurkat T cell line having PD-1 introduced therein or a control cell line having no (Mock) PD-1 introduced therein were co-cultured and thereafter the degree of apoptosis of the Jurkat T cells was evaluated by flow cytometry using Annexin-V.

(Results)

Figure 19:
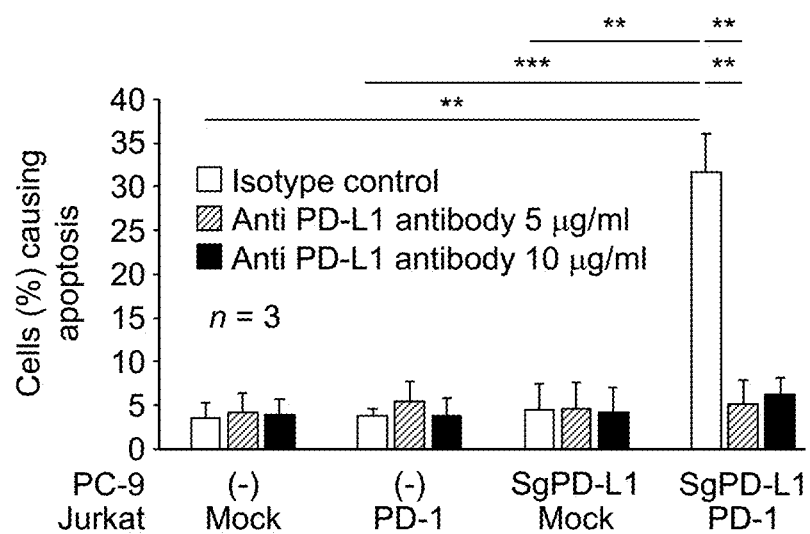
FIG. 19 shows that high expression of CD274 in association with a CD274 3'UTR abnormality induces apoptosis of PD-1 expressing T cells.

The results are shown in FIG. 19. "SgPD-L1" of "PC-9" in the horizontal axis indicates a PC-9 cell line in which high expression of CD274 in association with CD274 3'UTR abnormality was induced. The "(−)" indicates a PC-9 cell line in which high expression of CD274 in association with CD274 3'UTR abnormality was not induced. PD-1 of "Jurkat" in the horizontal axis indicates a Jurkat T cell line having PD-1 introduced therein and "Mock" indicates a control cell line in which PD-1 is not introduced.

It was shown that high expression of CD274 in association with CD274 3'UTR abnormality strongly induces apoptosis of T cells expressing PD-1 (the results of isotype control on the right in FIG. 19).

The results suggest that high expression of CD274 in association with CD274 3'UTR abnormality is responsible for escape from immunity.

18. High Expression of CD274 in Association with CD274 3'UTR Abnormality Promotes Tumorigenesis.

(Method)

To evaluate the effect of high expression of CD274 in association with CD274 3'UTR abnormality on tumorigenic potential in vivo, EG7-OVAcell line (SgPd-L1) in which high expression of CD274 in association with CD274 3'UTR abnormality was induced by the CRISPR-Cas9 system and a control cell line (Mock) were subcutaneously transplanted to the isogenic mice. An immunostimulating agent, poly (I:C) or PBS as a control was administered from 7th day after the transplantation and a tumor diameter was periodically measured. In this experiment, it is considered that poly (I: C) induces an immunity against a tumor (in particular ovalbumin).

(Results)

Figures 1, 20:
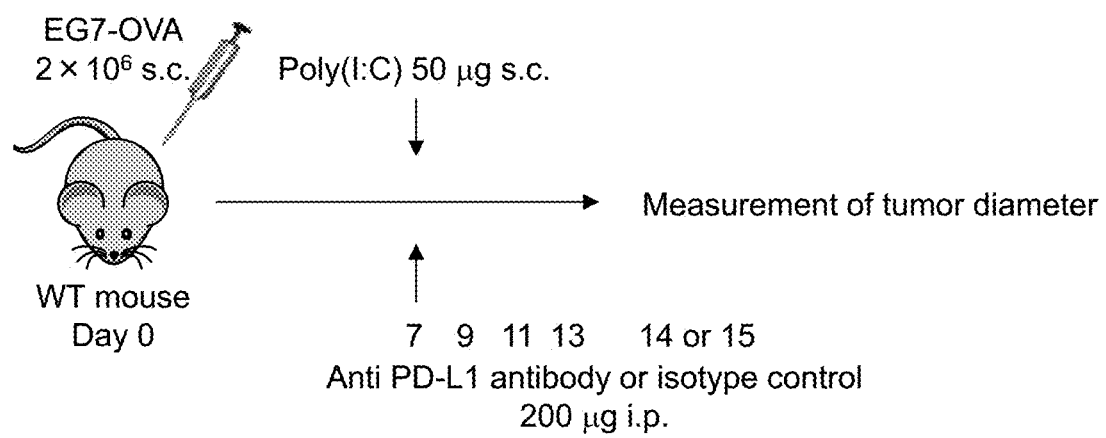
Figures 2, 20:
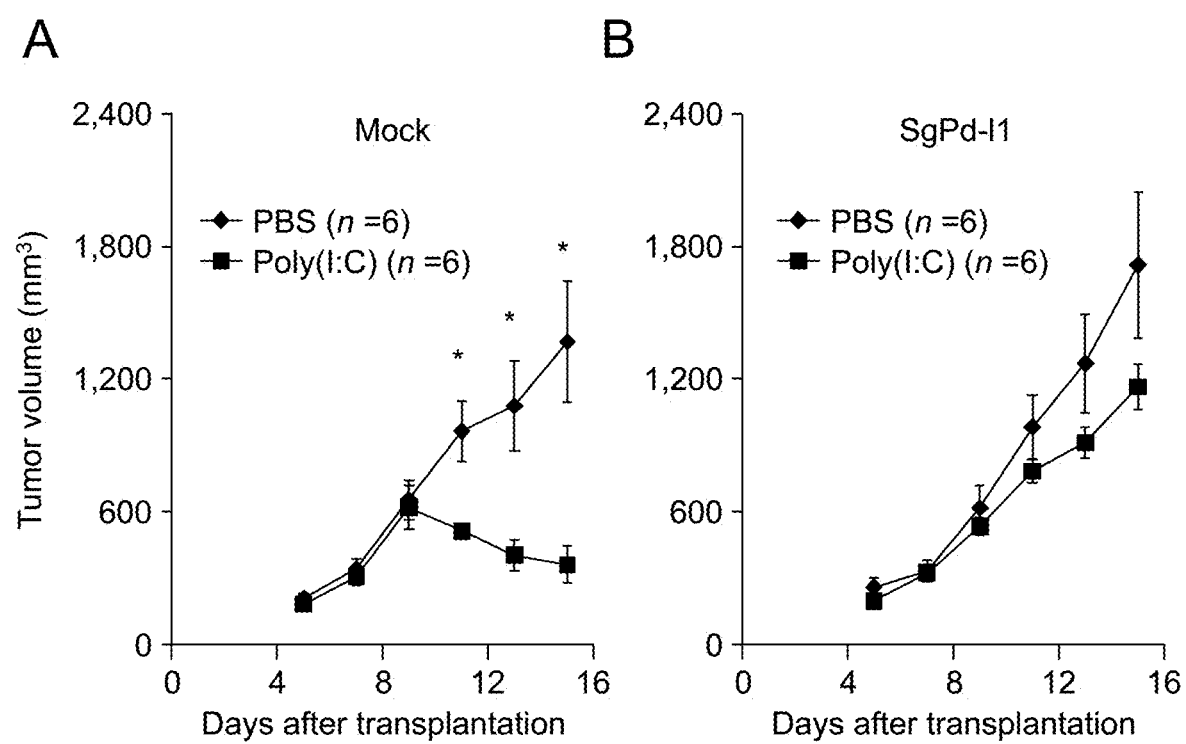

FIG. 20-1 shows the protocol of the experiment. FIG. 20-2 shows changes in tumor diameter; more specifically, a change in tumor diameter of Mock is shown in FIG. 20-2A and a change in tumor diameter of EG7-OVA cell line (SgPD-L1), in which high expression of CD274 was induced, is shown in FIG. 20-2B.

In the control cell line, a reduction in tumor diameter by administration of poly (I: C) was observed; however, in the cell line having high expression of CD274 in association with CD274 3'UTR abnormality, tumor increased, even if poly (I: C) was administered, to the same level as in the cell line to which poly (I: C) was not administered.

The results show that high expression of CD274 in association with CD274 3'UTR abnormality can overcome the tumor suppressing effect by antitumor immunity, in vivo.

19. High Expression of CD274 in Association with CD274 3'UTR Abnormality Suppresses Infiltration of CD8 Positive T Cells into Tumor.

(Method)

In the experiment of transplantation of EG7-OVA cell line to isogenic mice performed in the same manner as in Example 18, a tumor was taken from a mouse on 14 or 15th day after the transplantation and immuno-stained with CD8 and DAPI. In this manner, infiltration of CD8 positive T cells into the tumor was evaluated. The number of CD8 positive cells was counted in no less than 20 viewing fields of slices taken from representative 2 to 3 mice.

(Results)

Figures 1, 21:
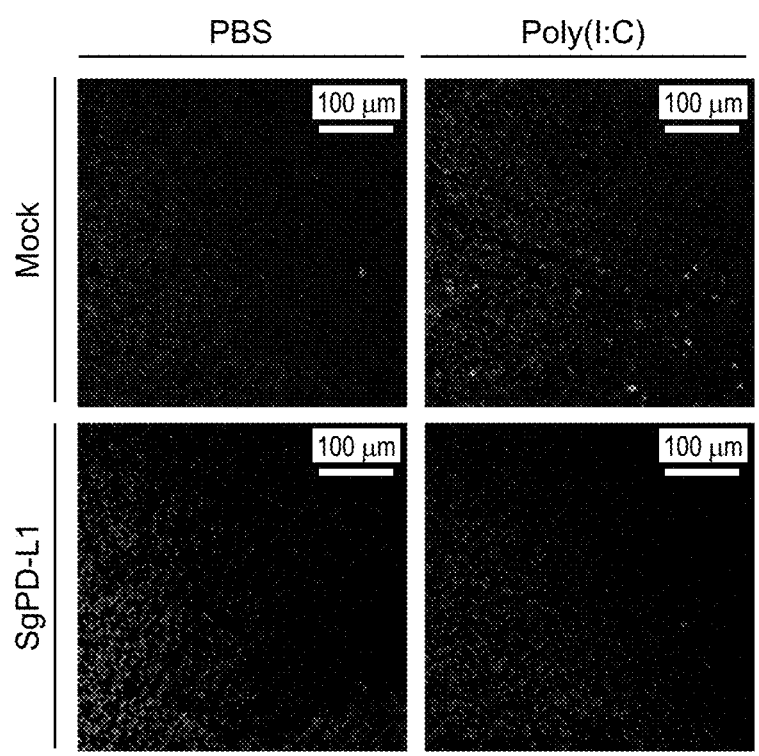
Figures 2, 21:
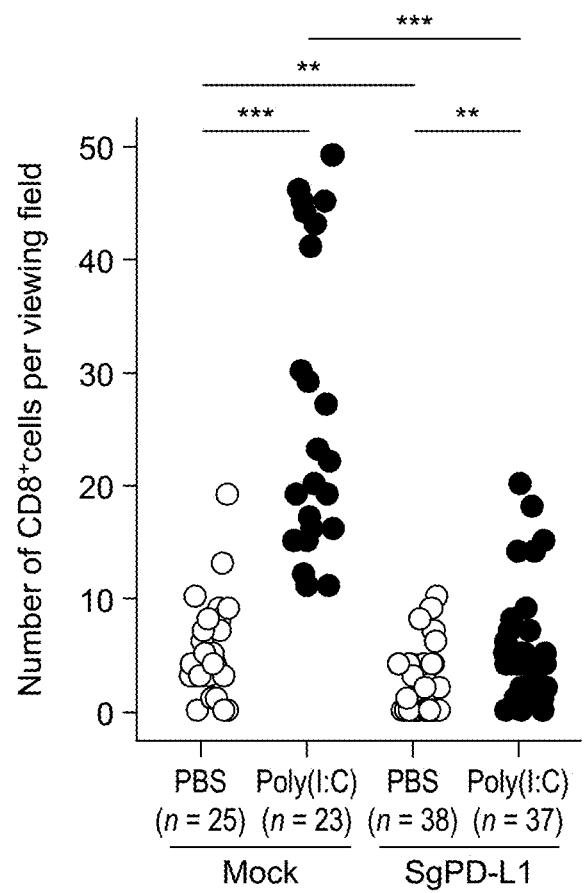

FIG. 21-1 shows stained images. FIG. 21-2 shows CD8 positive T cells within the tumor. Of the stained images of FIG. 21-1, in a stained image (upper right) of the control cell line (Mock) to which poly (I: C) was administered, the number of CD8 positive T cells stained green increases.

In the control cell line (Mock), infiltration of CD8 positive T cells into the tumor was increased by poly (I: C) administration; however, in the cell line (SgPD-L1) highly expressing CD274 in association with CD274 3'UTR abnormality, even if poly (I: C) was administered, the number of infiltrating cells only slightly increased.

The results suggest that high expression of CD274 in association with CD274 3'UTR abnormality has a suppressive effect of infiltration of CD8 positive cytotoxicity T cells into a tumor in vivo.

20. PD-1/PD-L1 Block can Suppress Promotion of Tumor Formation and Immunosuppressive Effect by High Expression of CD274 in Association with CD274 3'UTR Abnormality.

(Method)

To confirm the effect of PD-1/PD-L1 block against tumorigenic potential due to high expression of CD274 in association with CD274 3'UTR abnormality in vivo, an EG7-OVA cell line, in which high expression of CD274 in association with CD274 3'UTR abnormality was induced by CRISPR-Cas9 system, was subcutaneously transplanted to the isogenic mice. To mice to which an immunostimulating agent, poly (I: C), was administered, an anti PD-L1 antibody or an isotype control was intraperitoneally injected and the effect on the EG7-OVA tumor was evaluated. In these recipient mice, the diameter of a tumor was periodically measured. Fourteenth or fifteenth day after the transplantation, immunostaining with CD8 and DAPI were carried out to evaluate the extent of infiltration of CD8 positive T cells into the tumor.

(Results)

Figures 1, 22:
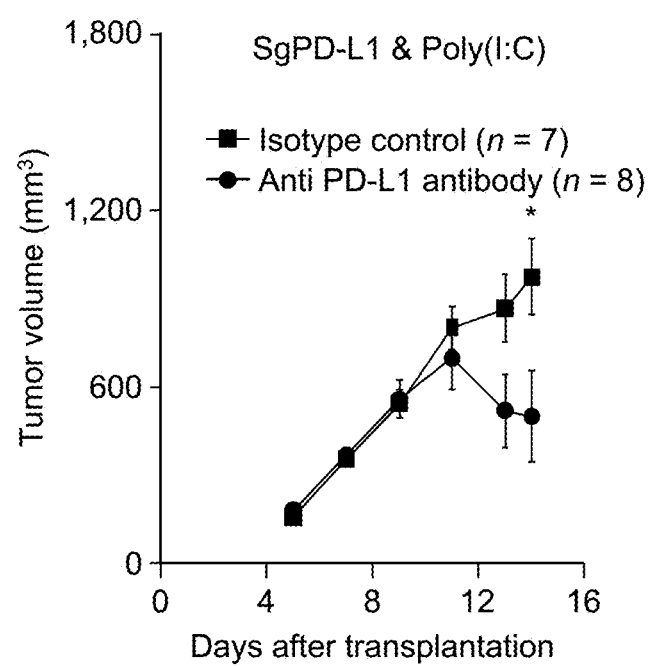
Figures 2, 22:
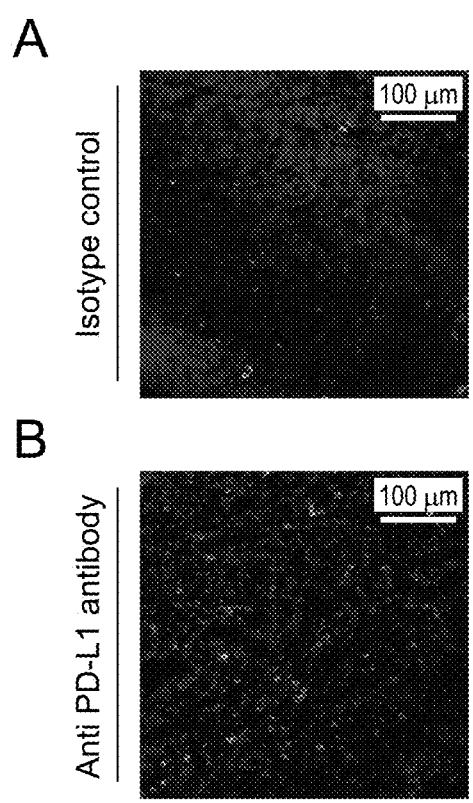
Figures 3, 22:
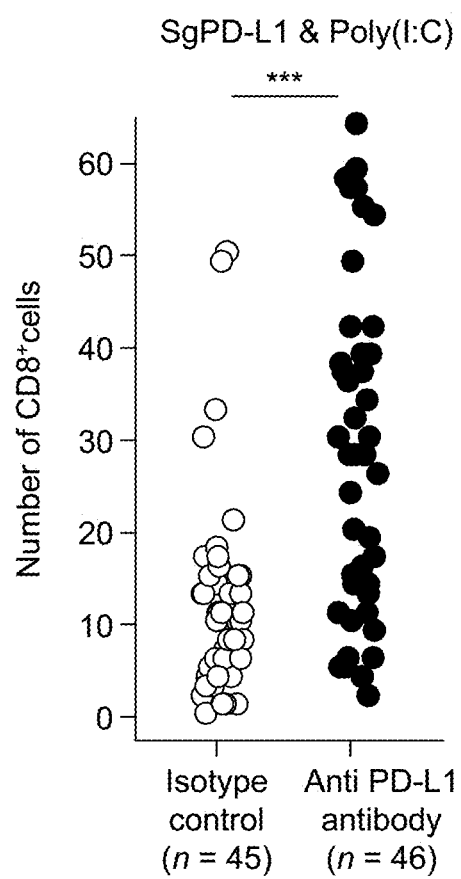

FIG. 22-1 is a graph showing a change of tumor diameter with time. FIG. 22-2 shows immunostained images with CD8 and DAPI. FIG. 22-3 shows CD8 positive T cells in a tumor. In the stained images in FIG. 22-2, the number of CD8 positive T cells stained green is larger in a mouse to which an anti PD-L1 antibody was administered (FIG. 22-3B) than in the mouse (FIG. 22-3A) to which an isotype control was administered.

As shown in the figures, it was found that tumorigenicity and infiltration of CD8 positive T cells into a tumor are suppressed by an anti PD-L1 antibody.

The results show that PD-1/PD-L1 block can suppress tumor formation and immunosuppressive effect due to high expression of CD274 in association with CD274 3'UTR abnormality in vivo.

21. Mutant in which a CD274 ORF was Truncated by CD274 SV Maintains PD-1 Binding Ability.

(Method)

Using ATL patient's specimens (5 specimens of ATL049, ATL050, ATL022 and ATL079) or a PC-9 cell line, to which CD274 wild type (WT) or a truncation mutant was introduced by a retrovirus, the binding ability to PD-1 Ig was evaluated by flow cytometry. Of the ATL patient's specimens, ATL050 had intact ORF (Intact) without truncation, ATL022 and ATL079 had a truncated ORF (Truncated). The mutant introduced into PC-9 was derived from ATL020 (defective Ex7) or ATL079 (defective Ex6 and 7).

(Results)

Figure 23:
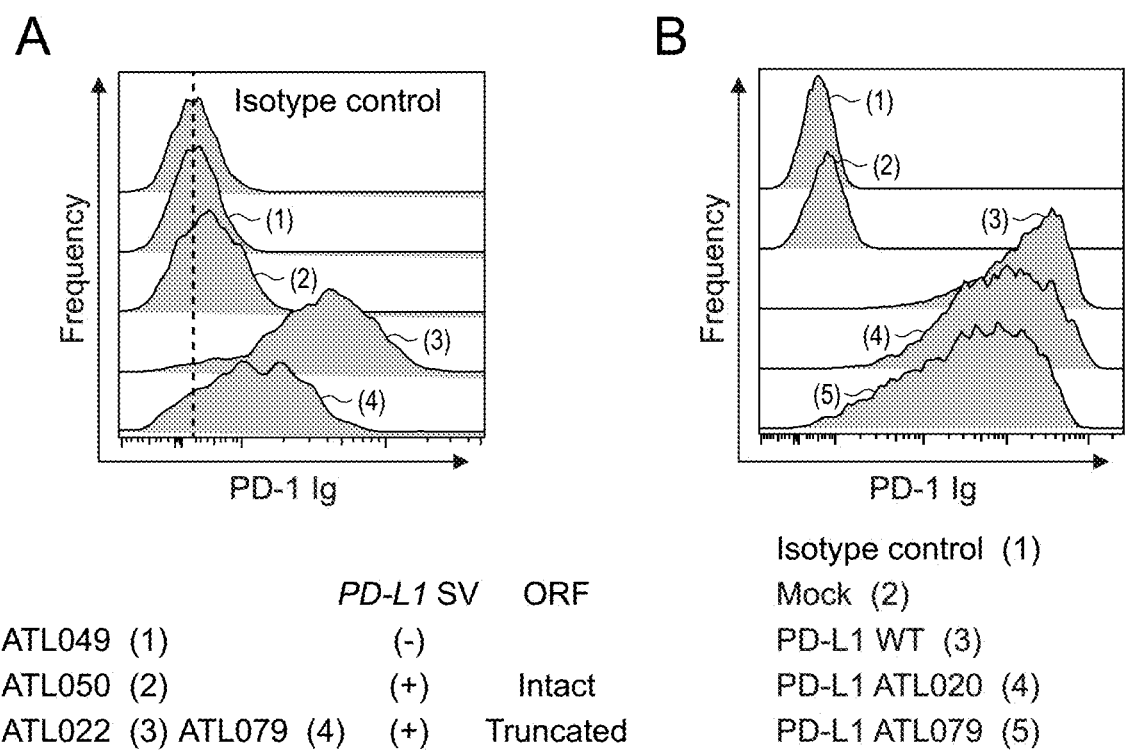
FIG. 23 shows PD-1 binding ability of a mutant whose CD274 open reading frame is truncated, based on flow cytometric evaluation.

FIG. 23 shows the results. FIG. 23A shows the evaluation results of ATL patient's specimens and FIG. 23B shows the results of the PC-9 cell line.

Either one of the ATL patient's specimens and CD274 gene-introduced PC-9 cell line, regardless of the intact or truncated ORF, binding to a receptor of PD-L1, i.e., PD-1, was confirmed.

The results show that PD-1 binding ability is not affected by truncation of CD274 ORF due to a CD274 structural abnormality and function of CD274 overexpressed as seen in CD274 SV (+) cases is maintained.

22. CD274 SV Relates to CD274 Overexpression Independently of the Number of Copies in the CD274 Region (Method)

Using DLBC 48 specimen and STAD415 specimen downloaded from TCGA and ATL43 specimen (experimental sample of the invention), how to relate CD274 expression (exon 4 RPKM) obtained by RNA sequencing analysis and the number of copies in the CD274 region obtained by SNP array with CD274 expression, was examined. As the statistical method, covariance analysis was employed.

(Results)

Figure 24:
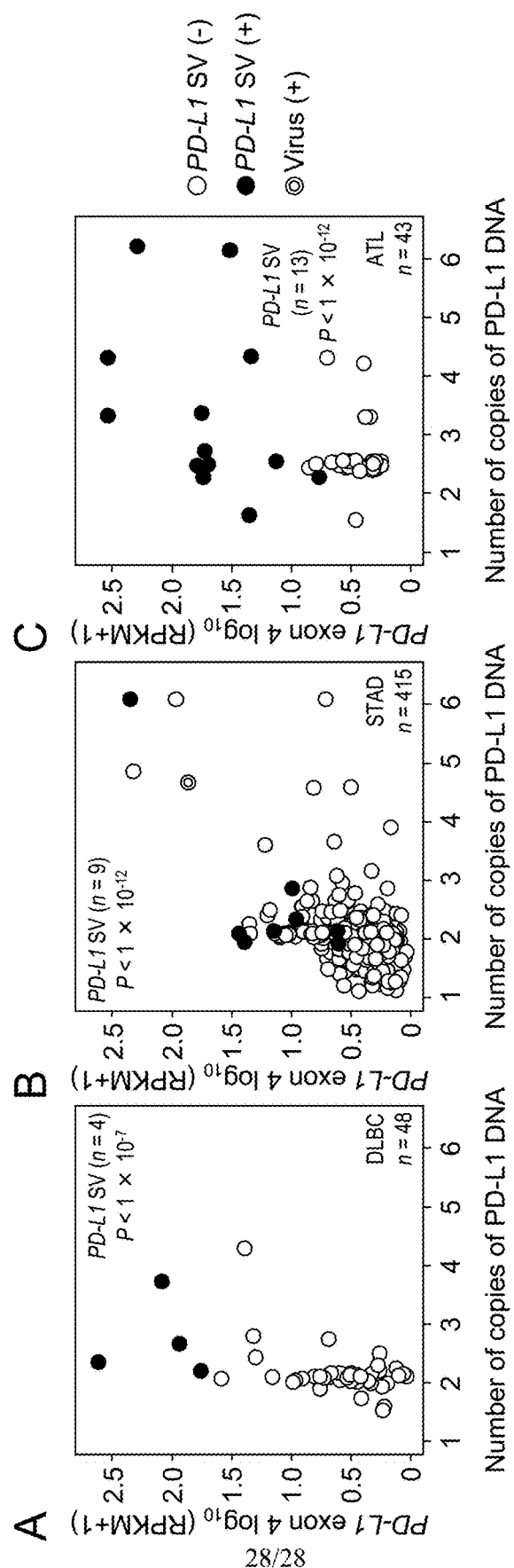
FIG. 24 shows graphs showing that a CD274 structural abnormality relates to CD274 overexpression independently of the number of copies of the CD274 region.

FIG. 24 shows the results. FIG. 24A shows the results of DLBC (B cellular lymphoma). FIG. 24B shows the results of STAD (stomach adenocarcinoma). FIG. 24C shows the results of ATL (adult T cell leukemia). In FIG. 24, solid circles represent the cases of CD274 fusion gene (+) and/or a relatively high CD274 exon 4/3'UTR ratio and double circles represent the cases of a virus insert (+) in the CD274 region.

In any one of DLBC, STAD and ATL, CD274 SV significantly independently related to high expression of CD274.

It is known that an increase in number of CD274 copies relates to high expression of CD274; however, the results demonstrate that CD274 SV relates to CD274 expression independently of the number of CD274 copies.

INDUSTRIAL APPLICABILITY

The present invention enables to determine the effectiveness of a PD-1/PD-L1 blockade in various types of cancers, and further determine the effectiveness of a PD-1/PD-L1 blockade per patient with a malignant tumor. As a result, the possibility of a PD-1/PD-L1 blockade in treatment of malignant tumors can be increased.

Sequence Listing Free Text

SEQ ID NO: 10, 11 primer.

The invention claimed is:

1. A method for treating a subject suffering from a malignant tumor, comprising
administering PD-1/PD-L1 blockade therapy to a subject having a tumor cell that is determined to have a complete or partial deletion in a 3' UTR region of a PD-L1 gene.

2. The method according to claim 1, wherein the deletion in 3'UTR region of the PD-L1 gene is induced by change in copy number of the PD-L1 gene.

3. The method according to claim 1, wherein a transcript of any one of exon 1 to exon 5 of the PD-L1 gene and a transcript of 3'UTR region of the PD-L1 gene have been quantified and a ratio between the amount of the transcript of the exon and the amount of the transcript of the 3'UTR region has been calculated.

4. The method according to claim 2, wherein a transcript of any one of exon 1 to exon 5 of the PD-L1 gene and a transcript of 3'UTR region of the PD-L1 gene have been quantified and a ratio between the amount of the transcript of the exon and the amount of the transcript of the 3'UTR region has been calculated.

5. The method according to claim 1, wherein a PD-L1 protein in a tumor cell taken from the subject is immunohistochemically stained using an anti-PD-L1 antibody that binds to a region that is downstream of exon 4 of PD-L1 and an anti-PD-L1 antibody that does not bind to the region that is downstream of exon 4 of PD-L1,
wherein the PD-1/PD-L1 blockade therapy is administered to the subject when the tumor cell
(a) becomes stained with the anti-PD-L1 antibody that does not bind to the region that is downstream of exon 4 of PD-L1, and
(b) does not become stained with the anti-PD-L1 antibody that binds to the region that is downstream of exon 4 of PD-L1.

6. The method according to claim 1, wherein the malignant tumor is selected from the group consisting of adult T-cell leukemia/adult T-cell leukemia lymphoma, stomach cancer, large intestinal cancer, bladder cancer, cervical cancer, renal cancer, lung adenocarcinoma, cutaneous malignant melanoma, and B cell lymphoma.

7. The method according to claim 2, wherein the malignant tumor is selected from the group consisting of adult T-cell leukemia/adult T-cell leukemia lymphoma, stomach cancer, large intestinal cancer, bladder cancer, cervical cancer, renal cancer, lung adenocarcinoma, cutaneous malignant melanoma, and B cell lymphoma.

8. The method according to claim 3, wherein the malignant tumor is selected from the group consisting of adult T-cell leukemia/adult T-cell leukemia lymphoma, stomach cancer, large intestinal cancer, bladder cancer, cervical cancer, renal cancer, lung adenocarcinoma, cutaneous malignant melanoma, and B cell lymphoma.

9. The method according to claim 4, wherein the malignant tumor is selected from the group consisting of adult T-cell leukemia/adult T-cell leukemia lymphoma, stomach cancer, large intestinal cancer, bladder cancer, cervical cancer, renal cancer, lung adenocarcinoma, cutaneous malignant melanoma, and B cell lymphoma.

10. The method according to claim 1, wherein the malignant tumor is selected from the group consisting of esophageal cancer, head and neck cancer, rectal cancer, and uterine body cancer.

11. The method according to claim 2, wherein the malignant tumor is selected from the group consisting of esophageal cancer, head and neck cancer, rectal cancer, and uterine body cancer.

12. The method according to claim 3, wherein the malignant tumor is selected from the group consisting of esophageal cancer, head and neck cancer, rectal cancer, and uterine body cancer.

13. The method according to claim 4, wherein the malignant tumor is selected from the group consisting of esophageal cancer, head and neck cancer, rectal cancer, and uterine body cancer.

14. The method according to claim 1, wherein the PD-1/PD-L1 blockade is anti PD-1 antibody or anti PD-L1 antibody.

15. The method according to claim 2, wherein the PD-1/PD-L1 blockade is anti PD-1 antibody or anti PD-L1 antibody.

16. The method according to claim 3, wherein the PD-1/PD-L1 blockade is anti PD-1 antibody or anti PD-L1 antibody.

17. The method according to claim 4, wherein the PD-1/PD-L1 blockade is anti PD-1 antibody or anti PD-L1 antibody.

18. The method according to claim 1, wherein a structural abnormality of tandem duplication, inversion, translocation or deletion in 9p24.1 region has been detected in association with the complete or partial deletion in 3'UTR region of PD-L1 gene.

19. The method according to claim 6, wherein the malignant tumor is adult T-cell leukemia/adult T-cell leukemia lymphoma.

20. The method according to claim 7, wherein the malignant tumor is adult T-cell leukemia/adult T-cell leukemia lymphoma.

21. The method according to claim 8, wherein the malignant tumor is adult T-cell leukemia/adult T-cell leukemia lymphoma.

22. The method according to claim 9, wherein the malignant tumor is adult T-cell leukemia/adult T-cell leukemia lymphoma.

* * * * *